(12) United States Patent
Wan et al.

(10) Patent No.: US 10,343,965 B2
(45) Date of Patent: Jul. 9, 2019

(54) SEPARATION OF DICHLOROPHENOLS

(71) Applicant: MONSANTO TECHNOLOGY LLC, Saint Louis, MO (US)

(72) Inventors: Kam-To Wan, Saint Louis, MO (US); Eduardo A. Casanova, Saint Louis, MO (US); John H. Ahn, Saint Louis, MO (US); Junqiu Yang, Saint Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 15/578,869

(22) PCT Filed: May 31, 2016

(86) PCT No.: PCT/US2016/034954
§ 371 (c)(1),
(2) Date: Dec. 1, 2017

(87) PCT Pub. No.: WO2016/196428
PCT Pub. Date: Dec. 8, 2016

(65) Prior Publication Data
US 2018/0179132 A1 Jun. 28, 2018

Related U.S. Application Data

(60) Provisional application No. 62/170,300, filed on Jun. 3, 2015.

(51) Int. Cl.
C02F 1/20 (2006.01)
C02F 1/26 (2006.01)
(Continued)

(52) U.S. Cl.
CPC ............... *C07C 37/72* (2013.01); *C02F 1/26* (2013.01); *C07C 37/74* (2013.01); *C07C 37/84* (2013.01);
(Continued)

(58) Field of Classification Search
None
See application file for complete search history.

(56) References Cited

U.S. PATENT DOCUMENTS 2,480,817 A 8/1949 Warren
2,651,659 A 9/1953 Warren et al.
(Continued)

FOREIGN PATENT DOCUMENTS

CN 1830942 A 9/2006
CN 101863744 A 10/2010
(Continued)

OTHER PUBLICATIONS

Twigg ("Dissociation Extraction" Nature, vol. 163, 1949, p. 1006-1007) (Year: 1949).*
(Continued)

*Primary Examiner* — Jafar F Parsa
*Assistant Examiner* — Amy C Bonaparte
(74) *Attorney, Agent, or Firm* — Stinson LLP; Erin C. Robert

(57) ABSTRACT

Various processes for the separation of a mixture containing dichlorophenols are described. In various aspects, the present invention relates to separation processes that produce an extract enriched in 2,4-dichlorophenol content and an extract enriched in 2,5-dichlorophenol content. The present invention further relates to various processes that integrate with these separation processes, such as a process for producing 3,6-dichloro-2-methoxybenzoic acid (dicamba)
(Continued)

or salt or ester thereof or a process for producing 2,4-dichlorophenoxyacetic acid (2,4-D) or salt or ester thereof.

20 Claims, 6 Drawing Sheets

(51) Int. Cl.

| | | |
|---|---|---|
| C02F 1/66 | (2006.01) | |
| C07C 37/72 | (2006.01) | |
| C07C 37/74 | (2006.01) | |
| C07C 37/84 | (2006.01) | |
| C07C 39/30 | (2006.01) | |
| C07C 51/09 | (2006.01) | |
| C07C 51/15 | (2006.01) | |
| C07C 65/05 | (2006.01) | |
| C07C 65/21 | (2006.01) | |
| C07C 67/31 | (2006.01) | |
| C07C 69/92 | (2006.01) | |
| C02F 101/34 | (2006.01) | |
| C02F 101/36 | (2006.01) | |
| C07C 51/347 | (2006.01) | |

(52) U.S. Cl.
CPC .............. *C07C 39/30* (2013.01); *C07C 51/09* (2013.01); *C07C 51/15* (2013.01); *C07C 51/347* (2013.01); *C07C 67/31* (2013.01); *C02F 1/20* (2013.01); *C02F 1/66* (2013.01); *C02F 2101/345* (2013.01); *C02F 2101/36* (2013.01)

(56) References Cited

U.S. PATENT DOCUMENTS

| | | | |
|---|---|---|---|
| 2,666,796 A | 1/1954 | Gorin et al. | |
| 2,708,209 A | 5/1955 | Nicolaisen et al. | |
| 3,013,054 A | 12/1961 | Richter | |
| 3,345,157 A | 10/1967 | Richter | |
| 3,389,969 A * | 6/1968 | Wirz | B01D 1/16 422/259 |
| 3,412,145 A | 11/1968 | Hanna | |
| 3,726,929 A | 4/1973 | Payne et al. | |
| 3,772,394 A | 11/1973 | Milnes | |
| 3,984,484 A | 10/1976 | Scremin et al. | |
| 4,001,341 A | 1/1977 | Welch et al. | |
| 4,161,611 A | 7/1979 | Kim | |
| 4,568,777 A * | 2/1986 | Baltes | C07C 37/00 568/774 |
| 4,754,080 A | 6/1988 | Butters et al. | |
| 5,118,876 A | 6/1992 | Zinnen et al. | |
| 5,648,562 A | 7/1997 | Henrick | |
| 2009/0076293 A1 | 3/2009 | Dux et al. | |

FOREIGN PATENT DOCUMENTS

| | | |
|---|---|---|
| CN | 102295552 A | 12/2011 |
| CN | 102838482 A | 12/2012 |
| CN | 102838483 A | 12/2012 |
| CN | 102942474 A | 2/2013 |
| CN | 103012123 A | 4/2013 |
| CN | 102125035 B | 7/2013 |
| GB | 1037573 A | 7/1966 |
| GB | 1316276 A | 5/1973 |

OTHER PUBLICATIONS

Robinson ("Ionization Constants of the Six Dichloroanilines and the Six Dichlorophenols in Aqueous Solution at 25C" Journal of Research of the National Bureau of Standards—A. Physics and Chemistry, vol. 68A, No. 2, Mar.-Apr. 1964, p. 159-164) (Year: 1964).*
Murray ("The Dissociation Constants of Some Chlorophenols" J. Am. Chem. Soc. 57, 1935, p. 110-111) (Year: 1935).*
Robbins ("Liquid-Liquid Extraction Operations and Equipment" Perry's Chemical Engineers' Handbook, 7th Edition, Chapter 15, 1999, p. 15-1 to 15-47) (Year: 1999).*
Stevens ("Extraction, Liquid-Liquid" Kirk-Othmer Encyclopedia of Chemical Technology, 2018, p. 1-60, DOI: 10.1002/0471238961. 120917211215.a01.pub3) (Year: 2018).*
Chen, X-M., et al., "Study on O-Alkylation for Synthesis of 3,6-Dichlorosalicylic Acid by Chloromethane," Henan chemical Industry, Jun. 2002, Abstract Only, 2 pages.
Eckstein, Z., et al., 1979, Przem Chem, 58/10:533-536, English Abstract Only, 1 page.
Es'Haghi, Z., "Extraction and Determination of Three Chlorophenols by Hollow Fiber Liquid Phase Microextraction—Spectrophotometric analysis, and Evaluation Procedures Using Mean Centering of Ratio Spectra Method," 2011, Am J Analyt Chem, 2:1-8, 8 pages.
Geankoplis, C.J., "Transport Processes and Unit Operations," 3rd Ed., 1993, Prentice Hall, Inc., A Simon & Schuster Company, Englewood Cliffs, NJ, p. 652, 4 pages.
Zhang, X., "The Synthesis of Herbicides Dicamba," 2002, Nongyao, 41/11:13-14, Abstract Only, 2 pages.
Zhang, Y., "Study on the Preparation of 3,6-Dichlorosalicylic Acid," 2002, Huangon Shikan, 16/12:45-48, Abstract Only, 1 page.
Zhang, Y., "The Study on the Preparation of Dicamba," 2002, Nongyao, 41/7:115-17, Abstract Only, 2 pages.
Zhu, J., et al., "Study on Separating Mixed Dichlorophenol by Cross-current Dissociation Extraction," 2012, Advanced Materials Research, 347-353:1255-1258, 5 pages.
Perry's Chemical Engineers' Handbook, 1984, 6th Ed., D.W. Green, Editor, McGraw-Hill Book Company, pp. 15-18-15-19, 4 pages.
Unit Operations of Chemical Engineering, 2001, 6th Ed., Warren L. McCabe et al., Editors, McGraw Hill, p. 648, 5 pages.
International Search Report and Written Opinion issued in PCT/2016/034954, dated Aug. 23, 2016, 9 pages.

* cited by examiner

SEPARATION OF DICHLOROPHENOLS

REFERENCE TO RELATED APPLICATIONS

The present application is the 371 National Stage Application of International Patent Application Serial No. PCT/US2016/034954, filed May 31, 2016, which claims the benefit of U.S. Provisional Application Ser. No. 62/170,300, filed Jun. 3, 2015, the entire contents of which are incorporated herein by reference.

FIELD OF THE INVENTION

The present invention generally relates to various processes for the separation of a mixture containing dichlorophenols. In various aspects, the present invention relates to separation processes that produce an extract enriched in 2,4-dichlorophenol content and an extract enriched in 2,5-dichlorophenol content. The present invention further relates to various processes that integrate with these separation processes, such as a process for producing 3,6-dichloro-2-methoxybenzoic acid (dicamba) or salt or ester thereof or a process for producing 2,4-dichlorophenoxyacetic acid (2,4-D) or salt or ester thereof.

BACKGROUND OF THE INVENTION

Dichlorophenols are useful intermediates in the preparation of a variety of chemical products. In particular, certain herbicides are prepared from dichlorophenols. For example, 2,4-dichlorophenoxyacetic acid (2,4-D) can be prepared from 2,4-dichlorophenol. See, for example, U.S. Pat. Nos. 2,480,817 and 2,651,659. Also, 3,6-dichloro-2-methoxybenzoic acid (dicamba) can be prepared from 2,5-dichlorophenol. See, for example, U.S. Pat. Nos. 3,013,054 and 5,648,562.

With the introduction of dicamba and 2,4-D tolerant traits in various crop plants, these herbicides are becoming increasingly important. Difficulties remain in processes for efficiently producing dicamba. High raw material cost, low process conversions and selectivities, and large amounts of wastes are problems that remain in these processes. In addition, the 2,5-dichlorophenol starting material is expected to significantly contribute to high raw material costs. Accordingly, there remains a need for improved processes in the production and separation of critical intermediates to dicamba, including 2,5-dichlorophenol, to improve process economics.

Processes for producing 2,4-D typically use 2,4-dichlorophenol as a starting material. However, processes used to prepare 2,4-dichlorophenol from phenol can produce mixtures of dichlorophenols. Accordingly, there remains a need for improved processes for separating 2,4-dichlorophenol from other dichlorophenols such as 2,6-dichlorophenol and/or 2,5-dichlorophenol to provide a relatively pure stream of 2,4-dichlorophenol suitable for the production of 2,4-D.

Mixtures of mono- and dichlorophenols, especially those containing 2,4-dichlorophenol and 2,5-dichlorophenol, are exceedingly difficult to separate by conventional distillation techniques since the boiling points of these compounds are within no more than few degrees centigrade of each other. U.S. Pat. No. 3,772,394 proposes an extraction process for selectively extracting with an aqueous alkaline solution a component of a mixture of 2,3-dichorophenol and 2,6-dichorophenol or a mixture of 2,5-, 2,4- and 3,4-isomers of dichorophenol. In this process, an extract is obtained in which the proportion of at least one of the dichlorophenols to another of the dichlorophenols is greater than in the feed mixture. However, this process fails to achieve significantly enriched fractions for more than one component of the feed mixture thereby requiring additional separation operations to recover more than one purified fraction. Thus, there remains a need for cost effective separation processes that can produce enriched fractions of multiple components of a chlorophenol feed mixture such as 2,4-dichlorophenol and 2,5-dichlorophenol.

SUMMARY OF THE INVENTION

The present invention relates to various separation processes for producing extracts of one or more dichlorophenols. Various aspects of the present invention include processes for producing an extract of 2,5-dichlorophenol and/or a salt thereof. Generally, these processes comprise feeding a chlorophenol feed mixture comprising 2,5-diclorophenol and 2,4-dichlorophenol to a fractional liquid-liquid extraction (FLLE) zone comprising a rectifying section and a stripping section; feeding an organic solvent to the stripping section of the FLLE zone; feeding an aqueous solution comprising base to the rectifying section of the FLLE zone; contacting the feed mixture with the organic solvent and the aqueous solution in the FLLE zone, wherein at least a portion of the 2,5-diclorophenol is transferred to an aqueous phase comprising the aqueous solution and at least a portion of the 2,4-dichlorophenol is transferred to an organic phase comprising the organic solvent; removing the aqueous extract comprising 2,5-dichlorophenol and/or a salt thereof in the aqueous phase from the stripping section of the FLLE zone, wherein the weight ratio of total 2,5-dichlorophenol to total 2,4-dichlorophenol in the aqueous extract is greater than the weight ratio of 2,5-dichlorophenol to 2,4-dichlorophenol in the chlorophenol feed mixture; and removing an organic extract comprising 2,4-dichlorophenol in the organic phase from the rectifying section of the FLLE zone.

Other aspects of the present invention include processes for producing an extract of 2,4-dichlorophenol. Generally, these processes comprise feeding a chlorophenol feed mixture comprising 2,4-diclorophenol and 2,5-dichlorophenol to a fractional liquid-liquid extraction (FLLE) zone comprising a rectifying section and a stripping section; feeding an organic solvent to the stripping section of the FLLE zone; feeding an aqueous solution comprising base to the rectifying section of the FLLE zone; contacting the feed mixture with the organic solvent and the aqueous solution in the FLLE zone, wherein at least a portion of the 2,4-dichlorophenol is transferred to an organic phase comprising the organic solvent and at least a portion of the 2,5-diclorophenol is transferred to an aqueous phase comprising the aqueous solution; removing the organic extract comprising 2,4-dichlorophenol in the organic phase from the rectifying section of the FLLE zone; and removing an aqueous extract comprising 2,5-dichlorophenol and/or a salt thereof in the aqueous phase from the stripping section of the FLLE zone, wherein the weight ratio of 2,4-dichlorophenol to 2,5-dichlorophenol in the organic extract is greater than the weight ratio of 2,4-dichlorophenol to 2,5-dichlorophenol in the chlorophenol feed mixture.

The present invention further relates to various processes that incorporate these separation processes.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
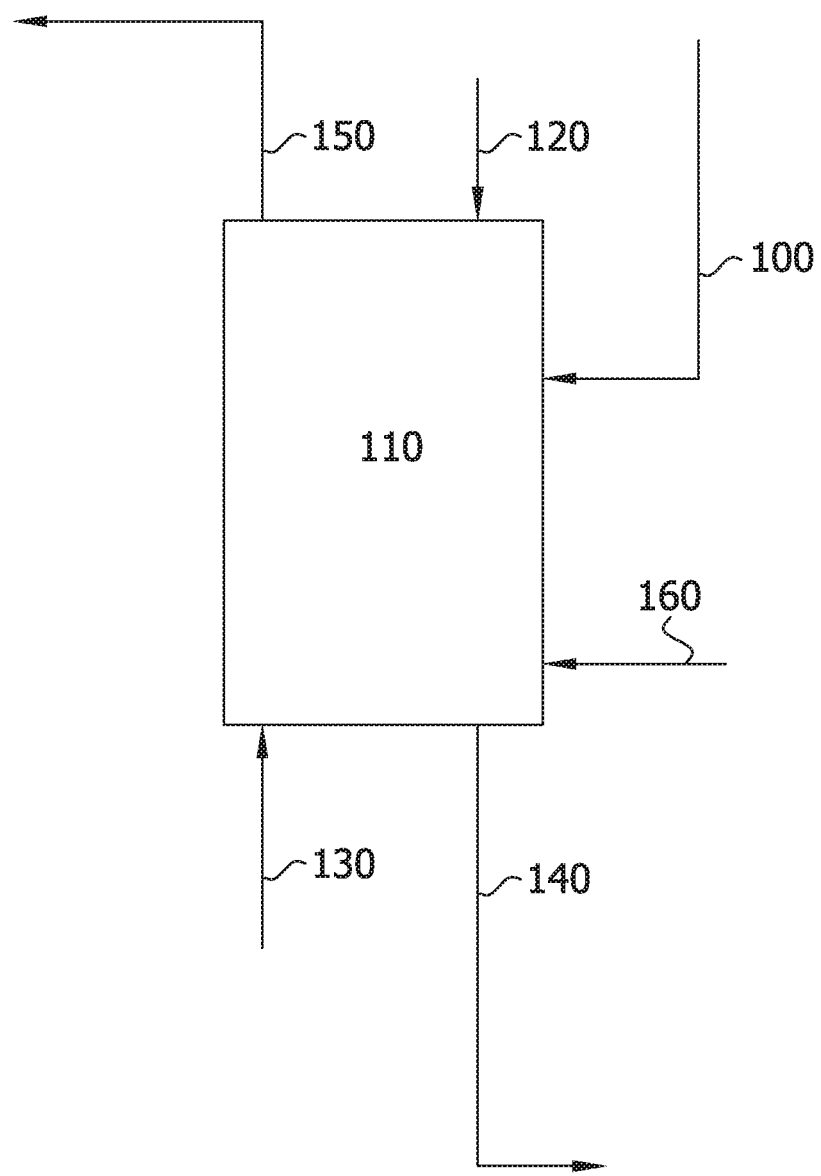
FIG. 1 presents a block flow diagram of a separation process in accordance with various aspects of the present invention.

In various aspects, the present invention relates to processes for separating a mixture containing dichlorophenols. Other aspects of the present invention relate to processes that are integrated with these separation processes, such as processes for producing 3,6-dichloro-2-methoxybenzoic acid (dicamba) or salt or ester thereof and processes for producing 2,4-dichlorophenoxyacetic acid (2,4-D) or salt or ester thereof.

Aspects of the present invention are directed to separation processes that produce an extract enriched in 2,4-dichlorophenol content and an extract enriched in 2,5-dichlorophenol content. These processes can advantageously produce enriched extracts of both components, which reduces or eliminates the need for additional operations to separate these components. Thus, separation processes in accordance with the present invention can significantly enhance process economics.

Further aspects of the present invention are directed to integrated processes that include any one of the dichlorophenol separation processes described herein. For example, various integrated processes include the isomerization of a feed of 2,4-dichlorophenol to 2,5-dichlorophenol and separation of the isomerization reaction product comprising a mixture of 2,4-dichlorophenol and 2,5-dichlorophenol. Efficient separation of the reaction mixture components permits recycle of unreacted 2,4-dichlorophenol, which significantly improves overall yield and process economics.

Processes in accordance with the present invention for producing an extract of dichlorophenols generally comprise fractional liquid-liquid extraction of a chlorophenol feed mixture.

Unless otherwise indicated, chlorophenols in an aqueous extract can be present in neutral forms and/or salt forms when an aqueous solution comprising base is used in the extraction. Typically, chlorophenolates (the anions of chlorophenols) are fully neutralized to chlorophenols during analysis (e.g. by RP-HPLC) as a part of the reported chlorophenol content. Accordingly, the total chlorophenol content in the aqueous extract refers to the sum of chlorophenols in both neutral and anion forms. For example, 2,5-dichlorophenol, 2,4-dichlorophenol, 2,6-dichlorophenol, and 2,3-dichlorophenol in an aqueous extract can be present as 2,5-dichlorophenol and/or a salt thereof, 2,4-dichlorophenol and/or a salt thereof, 2,6-dichlorophenol and/or a salt thereof, and 2,3-dichlorophenol and/or a salt thereof. The total 2,5-dichlorophenol in an aqueous extract refers to the sum of 2,5-dichlorophenol in both neutral and anion forms; the total 2,4-dichlorophenol in an aqueous extract refers to the sum of 2,4-dichlorophenol in both neutral and anion forms; the total 2,6-dichlorophenol in an aqueous extract refers to the sum of 2,6-dichlorophenol in both neutral and anion forms; and the total 2,3-dichlorophenol in an aqueous extract refers to the sum of 2,3-dichlorophenol in both neutral and anion forms.

Unless otherwise indicated, chlorophenols in an organic extract can be present substantially in neutral forms. For example, 2,4-dichlorophenol, 2,5-dichlorophenol, 2,3-dichlorophenol, 2-monochlorophenol, 3-monochlorophenol, and 4-monochlorophenol in an organic extract can be present substantially in neutral forms.

In the case of a chlorophenol feed mixture that further comprises salts of chlorophenols, the total chlorophenols in the chlorophenol feed mixture refer to the sum of chlorophenols in both neutral and anion forms. For example, in the case of the chlorophenol feed mixture further comprising salts of 2,4-dichlorophenol and 2,5-dichlorophenol, the 2,4-dichlorophenol in the chlorophenol feed mixture refers to the sum of 2,4-dichlorophenol in both neutral and anion forms; and the 2,5-dichlorophenol in the chlorophenol feed mixture refers to the sum of 2,5-dichlorophenol in both neutral and anion forms.

In various embodiments, the processes are directed to producing an aqueous extract comprising 2,5-dichlorophenol and/or a salt thereof. These processes generally comprise the following steps:

feeding a chlorophenol feed mixture comprising 2,5-diclorophenol and 2,4-dichlorophenol to a fractional liquid-liquid extraction (FLLE) zone comprising a rectifying section and a stripping section;

feeding an organic solvent to the stripping section of the FLLE zone;

feeding an aqueous solution comprising base to the rectifying section of the FLLE zone;

contacting the feed mixture with the organic solvent and the aqueous solution in the FLLE zone, wherein at least a portion of the 2,5-diclorophenol is transferred to an aqueous phase comprising the aqueous solution and at least a portion of the 2,4-dichlorophenol is transferred to an organic phase comprising the organic solvent;

removing the aqueous extract comprising 2,5-dichlorophenol and/or a salt thereof in the aqueous phase from the stripping section of the FLLE zone, wherein the weight ratio of total 2,5-dichlorophenol to total 2,4-dichlorophenol in the aqueous extract is greater than the weight ratio of 2,5-dichlorophenol to 2,4-dichlorophenol in the chlorophenol feed mixture; and removing an organic extract comprising 2,4-dichlorophenol in the organic phase from the rectifying section of the FLLE zone.

In further embodiments, processes of the present invention are directed to producing an organic extract comprising 2,4-dichlorophenol. Processes for producing an extract comprising 2,4-dichlorophenol generally comprise the following steps:

feeding a chlorophenol feed mixture comprising 2,4-diclorophenol and 2,5-dichlorophenol to a fractional liquid-liquid extraction (FLLE) zone comprising a rectifying section and a stripping section;

feeding an organic solvent to the stripping section of the FLLE zone;

feeding an aqueous solution comprising base to the rectifying section of the FLLE zone;

contacting the feed mixture with the organic solvent and the aqueous solution in the FLLE zone, wherein at least a portion of the 2,4-dichlorophenol is transferred to an organic phase comprising the organic solvent and at least a portion of the 2,5-diclorophenol is transferred to an aqueous phase comprising the aqueous solution;

removing the organic extract comprising 2,4-dichlorophenol in the organic phase from the rectifying section of the FLLE zone; and removing an aqueous extract comprising 2,5-dichlorophenol and/or a salt thereof in the aqueous phase from the stripping section of the FLLE zone, wherein the weight ratio of 2,4-dichlorophenol to 2,5-dichlorophenol in the organic extract is greater than the weight ratio of 2,4-dichlorophenol to 2,5-dichlorophenol in the chlorophenol feed mixture.

Various processes of the present invention can produce both an aqueous extract comprising 2,5-dichlorophenol and/or a salt thereof and an organic extract comprising 2,4-dichlorophenol wherein the weight ratio of total 2,5-dichlorophenol to total 2,4-dichlorophenol in the aqueous extract is greater than the weight ratio of 2,5-dichlorophenol to 2,4-dichlorophenol in the chlorophenol feed mixture and the weight ratio of 2,4-dichlorophenol to 2,5-dichlorophenol in the organic extract is greater than the weight ratio of 2,4-dichlorophenol to 2,5-dichlorophenol in the chlorophenol feed mixture.

A block flow diagram illustrating a process in accordance with the present invention is provided in FIG. 1. Referring to FIG. 1, a chlorophenol feed mixture 100 comprising 2,5-diclorophenol and 2,4-dichlorophenol is fed to FLLE zone 110. The FLLE zone comprises a series of stages and/or theoretical stages in the case of a packed column, and the chlorophenol feed mixture 100 is fed to an intermediate stage. In this process, the stages above the feed location define a rectifying section of the FLLE zone 110 while the stages below the feed stage define a stripping section (in the context of a vertical arrangement). Generally, the rectifying and stripping sections each comprise at least one stage and each typically comprises a series of stages or theoretical stages.

An aqueous solution 120 comprising a base is fed to the rectifying section of the FLLE zone. Also, an organic solvent 130 is fed to the stripping section of the FLLE zone. The chlorophenol feed mixture is contacted with the organic solvent and aqueous solution in the FLLE zone 110. The FLLE system partitions components of the chlorophenol feed mixture based on each component's respective pKa, with the lower pKa components generally partitioning towards the aqueous phase and ultimately exiting the stripping section of the FLLE zone (as aqueous extract 140), and the higher pKa components generally partitioning towards the organic phase ultimately exiting the rectifying section of the FLLE zone (as organic extract 150). The pKa of 2,5-dichlorophenol is 7.51 while the pKa of 2,4-dichlorophenol is 8.09. Thus, in the FLLE zone, contact of the chlorophenol feed mixture with the organic solvent and aqueous solution causes at least a portion of the 2,5-diclorophenol to be transferred to the aqueous phase to form aqueous extract 140 and at least a portion of the 2,4-dichlorophenol to be transferred to the organic phase to form organic extract 150.

Typically, the organic solvent is fed at the end or near the end of the stripping section (i.e., near to where the aqueous extract is withdrawn from the FLLE zone). In a FLLE zone that is positioned vertically (e.g., a vertical column) as generally depicted in FIG. 1, the organic solvent is fed into the bottom or a stage that is positioned within a lower portion of the stripping section.

The organic solvent can be an aromatic solvent, aliphatic solvent, or a mixture thereof. In various embodiments, the organic solvent comprises an aromatic solvent. Aromatic solvents include, for example of benzene, toluene, xylenes, and mixtures thereof. In one embodiment, the aromatic solvent comprises xylenes (e.g., a mixture of xylene isomers).

The organic solvent can include an aliphatic solvent. Aliphatic solvents include alkyl, dialkyl ether, or halogenated alkyl solvents. Alkyl solvents can be selected from the group consisting of hexane, heptane, octane, and mixtures thereof. Dialkyl ether solvents have a general formula of R—O—R', wherein R and R' are each independently a $C_1$-$C_6$ alkyl. For example, the dialkyl ether solvent can be selected from the group consisting of methyl butyl ether, dibutyl ether, cyclopentyl methyl ether, and mixtures thereof.

Some solvents such as certain halogenated solvents including dichloroethane, chloroform, and carbon tetrachloride have a higher density than water. Therefore, when dense organic solvents are used as the organic solvent, the aqueous solution comprising base is fed to the stripping section of the FLLE zone while the dense organic solvent is fed to the rectifying section. Consequently, in these alternative embodiments, the aqueous extract is removed from the rectifying section and the organic extract is removed from the stripping section.

An excess or at least an equivalent amount of organic solvent can be used as compared to the amount of the chlorophenol feed mixture fed to the FLLE zone on a weight basis. Accordingly, the weight ratio of organic solvent (e.g., xylenes) to the chlorophenol feed mixture fed to the FLLE zone can be from about 1:1 to about 15:1, from about 2:1 to about 10:1, from about 3:1 to about 10:1, or from about 3:1 to about 7:1.

The aqueous solution comprising base is typically fed at the end or near the end of the rectifying section (i.e., near where the organic extract is withdrawn from the FLLE zone). In a FLLE zone that is positioned vertically (e.g., a vertical column) as generally depicted in FIG. 1, the aqueous solution comprising a base is fed into the top or a stage that is positioned within the upper portion of the rectifying section. In a FLLE zone that comprises a series of mixer-settler vessels arranged horizontally or vertically, the term "upper portion" as used herein refers to vessels that are positioned near the inlet of the aqueous solution comprising base and outlet of the organic extract.

A variety of bases can be used including an alkali or alkaline earth hydroxide, carbonate, or bicarbonate. The molar ratio of base (e.g., potassium hydroxide) to 2,5-dichlorophenol in the dichlorophenol feed mixture can be in the range from about 0.5:1 to about 5:1, from about 0.5:1 to about 3:1, from about 0.9:1 to about 3:1, from about 1.5:1 to about 3:1, or from about 2:1 to about 3:1. In various embodiments, the base comprises potassium hydroxide. An aqueous solution of potassium hydroxide can have, for example, a concentration of from about 1 wt. % to about 10 wt. %, from about 2 wt. % to about 7 wt. %, from about 3 wt. % to about 7 wt. %, from about 3 wt. % to about 5 wt. %, or from about 2 wt. % to about 5 wt. %.

Referring again to FIG. 1, an aqueous solution 160 comprising acid can be fed to the stripping section of the FLLE zone 110. Without being bound by theory, adding acid in the stripping section in combination with the addition of base to the rectifying section produces a pH gradient within the FLLE zone that enhances the partitioning of 2,4-dichlorophenol and 2,5-dichlorophenol. Thus, various embodiments of the present invention further comprise feeding an aqueous solution comprising acid to the stripping section of the FLLE zone.

The aqueous solution comprising acid is fed into a stage of the stripping section that is positioned within a lower portion of the stripping section, but preferably at a high enough stage to provide sufficient mixing. Accordingly, in various configurations of the FLLE zone, the acid is fed into a stage that is positioned in the lower 5% to 25%, 10% to 25%, or 10% to 20% of the stripping section. In a FLLE zone that comprises a series of mixer-settler vessels arranged horizontally or vertically, the term "lower portion" as used herein refers to vessels that are positioned near the inlet of the organic solvent and outlet of the aqueous extract.

A wide variety of acids can be used. For example, the acid can be a mineral acid or an organic acid. Suitable mineral acids include, for example, hydrochloric acid, sulfuric acid, and phosphoric acid. Organic acids include, for example, formic acid, acetic acid, propionic acid, butyric acid, citric acid, and mixtures thereof. In various embodiments, the acid is hydrochloric acid. The acid can be fed to the FLLE zone as an aqueous solution. In various embodiments, the aqueous solution of hydrochloric acid has a concentration of from about 5 wt. % to about 30 wt. %, from about 10 wt. % to about 30 wt. %, from about 15 wt. % to about 30 wt. %, from about 20 wt. % to about 30 wt. %, from about 25 wt. % to about 30 wt. %, from about 10 wt. % to about 25 wt. %, from about 15 wt. % to about 25 wt. %, or from about 20 wt. % to about 25 wt. %.

The amount of acid fed to the stripping section of the FLLE zone can be quantified based on the amount of base fed to the rectifying section of the FLLE zone. Accordingly, the molar ratio of acid to base can be in the range from about 0.5:1 to about 2:1, from about 0.5:1 to about 1:1, or from about 0.6:1 to about 0.8:1.

Also, the pH of the aqueous extract comprising 2,5-dichlorophenol and/or a salt thereof in the aqueous phase withdrawn from the stripping section can be controlled by the amount of base and/or acid added to the FLLE zone. As such the pH of the aqueous extract comprising 2,5-dichlorophenol and/or a salt thereof in the aqueous phase exiting the stripping section can be maintained between about 8 and about 9, between about 8.2 and about 8.8, or between about 8.4 and about 8.8. The pH of the aqueous phase contacting the organic extract comprising 2,4-dichlorophenol in the organic phase exiting the rectifying section (e.g., at a location near or at the feed of the aqueous solution comprising base) is greater than the pH of the aqueous extract comprising 2,5-dichlorophenol and/or a salt thereof in the aqueous phase exiting the stripping section. Accordingly, the pH of the aqueous phase contacting the organic extract comprising 2,4-dichlorophenol in the organic phase exiting the rectifying section can be maintained between about 9 and about 10.5, between about 9.5 and about 10.5, or between about 9.5 and about 10.

The separation processes of the present invention can be used to separate a variety of feed mixtures comprising 2,5-dichlorophenol and 2,4-dichlorophenol. For example, the chlorophenol feed mixture can be obtained from an isomerization process where 2,4-dichlorophenol is isomerized to 2,5-dichlorophenol. The concentrations of 2,5- and 2,4-dichlorophenol can fall within a wide range. In various embodiments, the 2,5-dichlorophenol concentration in the chlorophenol feed mixture is at least about 5 wt. %, at least about 10 wt. %, at least about 20 wt. %, at least about 30 wt. %, at least about 40 wt. %, or at least about 50 wt. % of the total chlorophenol content. The 2,5-dichlorophenol concentration in the chlorophenol feed mixture can be from about 5 wt. % to about 80 wt. %, from about 5 wt. % to about 70 wt. %, from about 5 wt. % to about 60 wt. %, from about 10 wt. % to about 80 wt. %, from about 10 wt. % to about 70 wt. %, from about 10 wt. % to about 60 wt. %, from about 20 wt. % to about 70 wt. %, from about 20 wt. % to about 60 wt. %, from about 30 wt. % to about 70 wt. %, from about 30 wt. % to about 60 wt. %, from about 40 wt. % to about 70 wt. %, or from about 40 wt. % to about 60 wt. % of the total chlorophenol content.

In various embodiments, the 2,4-dichlorophenol concentration in the chlorophenol feed mixture is at least about 5 wt. %, at least about 10 wt. %, at least about 20 wt. %, at least about 30 wt. %, at least about 40 wt. %, or at least about 50 wt. % of the total chlorophenol content. The 2,4-dichlorophenol concentration in the chlorophenol feed mixture can be from about 10 wt. % to about 90 wt. %, from about 10 wt. % to about 80 wt. %, from about 20 wt. % to about 80 wt. %, from about 30 wt. % to about 80 wt. %, from about 20 wt. % to about 50 wt. %, from about 30 wt. % to about 50 wt. %, from about 30 wt. % to about 40 wt. %, from about 35 wt. % to about 50 wt. %, or from about 35 wt. % to about 45 wt. % of the total chlorophenol content.

In some embodiments, the weight ratio of 2,4-dichlorophenol to 2,5-dichlorophenol in the chlorophenol feed mixture fed to the FLLE zone can be from about 1:1 to about 5:1, from about 1:1 to about 4:1, from about 1.5:1 to about 5:1, from about 2:1 to about 4:1, from about 2.5:1 to about 3.5:1, or about 3:1.

The chlorophenol feed mixture can also be obtained from phenol chlorination processes that produce a mixture of dichlorophenols comprising 2,4-dichlorophenol. For example, see U.S. Pat. No. 4,754,080. For example, the chlorophenol feed mixture can comprise 2,4-dichlorophenol, 2- and/or 4-monochlorophenol, 2,6-dichlorophenol, and 2,4,6-trichlorophenol. In some embodiments, the chlorophenol feed mixture can be substantially free of 2,5-dichlorophenol. In various embodiments, the 2,5-dichlorophenol can be a part of the chlorophenol feed mixture when the 2,4-dichlorophenol undergoes via isomerization to form a small portion of 2,5-dichlorophenol. Accordingly, the weight ratio of 2,4-dichlorophenol to 2,5-dichlorophenol in the chlorophenol feed mixture fed to the FLLE zone can be from about 10:1 to about 200:1, from about 10:1 to about 100:1, from about 10:1 to about 50:1, from about 20:1 to about 200:1, from about 20:1 to about 100:1, or from about 20:1 to about 50:1. The 2,4-dichlorophenol concentration in the chlorophenol feed mixture can be at least about 50 wt. %, at least about 60 wt. %, at least about 70 wt. %, at least about 80 wt. %, or at least about 90 wt. % of the total chlorophenol content. For example, the 2,4-dichlorophenol concentration in the chlorophenol feed mixture can be from about 50 wt. % to about 95 wt. %, from about 50 wt. % to about 90 wt. %, from about 50 wt. % to about 80 wt. %, from about 60 wt. % to about 95 wt. %, from about 60 wt. % to about 90 wt. %, from about 60 wt. % to about 80 wt. %, from about 70 wt. % to about 95 wt. %, from about 70 wt. % to about 90 wt. %, from about 70 wt. % to about 80 wt. %, from about 80 wt. % to about 95 wt. %, or from about 80 wt. % to about 90 wt. % of the total chlorophenol content.

Also, in some embodiments, the 2,5-dichlorophenol concentration in the chlorophenol feed mixture can be relatively low. For example, the 2,5-dichlorophenol concentration can be less than about 10 wt. %, or less than about 5 wt. % of the total chlorophenol content. In these and other embodiments, the 2,5-dichlorophenol concentration can be within the range from about 0.5 wt. % to about 10 wt. %, from about 0.5 wt. % to about 5 wt. %, from about 1 wt. % to about 10 wt. %, from about 1 wt. % to about 5 wt. %, or from about 5 wt. % to about 10 wt. % of the total chlorophenol content.

As discussed further herein, the chlorophenol feed mixture can further comprise salts of 2,4-dichlorophenol and 2,5-dichlorophenol such as potassium salts. The chlorophenol feed can also comprise other mono-, di-, and trichlorophenols. In various embodiments, the chlorophenol feed mixture can comprise 2-, 3-, and/or 4-monochlorophenol. In some embodiments, the chlorophenol feed mixture can comprise at least one monochlorophenol selected from the group consisting of 2-monochlorophenol, 4-monochlorophenol, and combinations thereof. Further, the chlorophenol feed mixture can comprise 2,3-dichlorophenol; 2,6-dichlorophenol; and/or 3,4-dichlorophenol. In various embodiments, 2,6-dichlorophenol and 3,4-dichlorophenol constitute less than about 5 wt. %, less than about 2.5 wt. %, or less than about 1 wt. % of the dichlorophenol content of the chlorophenol feed mixture. Depending on the source, the feed mixture can also include one or more trichlorophenols such as 2,4,6-trichlorophenol.

Various separation processes of the present invention produce an extract that is enriched in 2,5-dichlorophenol and/or a salt thereof. Accordingly, processes of the present invention generally provide an extract that is enriched in total 2,5-dichlorophenol relative to total 2,4-dichlorophenol as compared to the same weight ratio in the chlorophenol feed. In various embodiments, the weight ratio of total 2,5-dichlorophenol to total 2,4-dichlorophenol in the aqueous extract is at least about 10:1 or at least about 15:1. The weight ratio of total 2,5-dichlorophenol to total 2,4-dichlorophenol in the aqueous extract can be from about 10:1 to 200:1, from about 15:1 to about 200:1, from about 20:1 to about 200:1, from about 10:1 to about 100:1, from about 15:1 to about 100:1, or from about 20:1 to about 100:1.

Further, various separation processes of the present invention produce an extract that is enriched in 2,5-dichlorophenol and/or a salt thereof relative to the total chlorophenol content in the aqueous extract. In various embodiments, the total 2,5-dichlorophenol content in the aqueous extract can be at least about 50 wt. %, at least about 60 wt. %, at least about 70 wt. %, at least about 80 wt. %, or at least about 90 wt. % of the total chlorophenol content in the aqueous extract. The total 2,5-dichlorophenol content in the aqueous extract can be from about 55 wt. % to about 99 wt. %, from about 60 wt. % to about 99 wt. %, from about 70 wt. % to about 99 wt. %, from about 80 wt. % to about 99 wt. %, from about 90 wt. % to about 99 wt. %, from about 55 wt. % to about 90 wt. %, from about 60 wt. % to about 90 wt. %, from about 70 wt. % to about 90 wt. %, from about 65 wt. % to about 85 wt. %, or from about 70 wt. % to about 80 wt. % of the total chlorophenol content in the aqueous extract.

The separation processes of the present invention can also produce an organic extract that is enriched in 2,4-dichlorophenol. Accordingly, processes of the present invention can provide an organic extract that is enriched in 2,4-dichlorophenol relative to 2,5-dichlorophenol as compared to the same weight ratio in the feed. In various embodiments, the weight ratio of 2,4-dichlorophenol to 2,5-dichlorophenol in the organic extract is at least about 1.5:1, at least about 2:1, at least about 5:1, at least about 10:1, at least about 20:1, at least about 50:1 or higher. The weight ratio of 2,4-dichlorophenol to 2,5-dichlorophenol in the organic extract can be from about 1.5:1 to 100:1, from about 1.5:1 to about 50:1, from about 1.5:1 to about 20:1, from about 1.5:1 to 10:1, from about 2:1 to about 100:1, from about 2:1 to about 50:1, from about 2:1 to about 20:1, from about 2:1 to 10:1, from about 5:1 to about 100:1, from about 5:1 to about 50:1, from about 5:1 to about 20:1, from about 5:1 to 10:1, from about 10:1 to about 100:1, from about 10:1 to about 50:1, or from about 10:1 to about 20:1.

Further, processes of the present invention can provide an organic extract that is enriched in 2,4-dichlorophenol relative to the total chlorophenol content in the organic extract. In various embodiments, the 2,4-dichlorophenol content in the organic extract can be at least about 50 wt. %, at least about 60 wt. %, at least about 70 wt. %, at least about 80 wt. %, or at least about 90 wt. % of the total chlorophenol content in the organic extract. The 2,4-dichlorophenol content in the organic extract can be from about 55 wt. % to about 95 wt. %, from about 60 wt. % to about 95 wt. %, from about 60 wt. % to about 90 wt. %, from about 70 wt. % to about 95 wt. %, from about 70 wt. % to about 90 wt. %, from about 70 wt. % to about 85 wt. %, from about 75 wt. % to about 95 wt. %, from about 75 wt. % to about 90 wt. %, or from about 80 wt. % to about 90 wt. % of the total chlorophenol content in the organic extract. In some embodiments, wherein the chlorophenol feed mixture is obtained from phenol chlorination processes and the 2,5-dichlorophenol concentration in the chlorophenol feed mixture is relatively low, the 2,4-dichlorophenol content in the organic extract can be from about 60 wt. % to about 99 wt. %, from about 70 wt. % to about 99 wt. %, from about 75 wt. % to about 99 wt. %, or from about 80 wt. % to about 99 wt. % of the total chlorophenol content in the organic extract.

The separation processes of the present invention produce enhanced recovery of the 2,5-dichlorophenol and 2,4-dichlorophenol from various chlorophenol feed mixtures. A portion of 2,5-dichlorophenol may partition in the organic phase as part of the organic extract comprising 2,4-dichlorophenol. Therefore, the recovery of total 2,5-dichlorophenol in the aqueous extract may be from about 60 wt. % to about 90 wt. % of the 2,5-dichlorophenol content in the chlorophenol feed mixture. As a comparison, the recovery of 2,4-dichlorophenol in the organic extract may be higher due to the lower pH gradient in the aqueous phase exiting the rectifying section, which may allow 2,4-dichlorophenol to be completely partitioned in the organic phase. Accordingly, the recovery of 2,4-dichlorophenol in the organic extract may be from 70 wt. % to about 99 wt. % of the 2,4-dichlorophenol content in the chlorophenol feed mixture.

The enhanced recovery of 2,5-dichlorophenol and 2,4-dichlorophenol, as described above, in the separation processes of the present invention has advantages over other separation processes known in the art, such as distillation. If even possible, distillation processes would require additional equipment and higher temperatures to achieve a comparable separation of 2,5-dichlorophenol and 2,4-dichlorophenol. In addition, high temperatures generated during the distillation may also produce undesirable side products.

As noted above, the chlorophenol feed mixture can further comprise 2,6-dichlorophenol. The pKa of 2,6-dichlorophenol is 6.79, which is less than that for 2,5-dichlorophenol. Thus, when present in the feed mixture, 2,6-dichlorophenol will generally partition in the aqueous extract along with 2,5-dichlorophenol. As such, the aqueous extract comprising 2,5-dichlorophenol and/or a salt thereof in the aqueous phase can further comprise 2,6-dichlorophenol and/or a salt thereof. Accordingly, the organic extract comprising 2,4-dichlorophenol in the organic phase can be substantially free of 2,6-dichlorophenol. In various embodiments, as discussed further herein, 2,6-dichlorophenol can be substantially removed from the feed mixture prior to the FLLE zone. Therefore, in these and other embodiments, total 2,6-dichlorophenol can constitute no more than about 3 wt. %, no more than about 2 wt. %, no more than about 1 wt. %, or no more than about 0.5 wt. % of the total chlorophenol content of the aqueous extract. For example, total 2,6-dichlorophenol can constitute from about 0.1 wt. % to about 3 wt. %, from about 0.1 wt. % to 2 wt. %, from about 0.1 wt. % to about 1 wt. %, from about 0.1 wt. % to about 0.5 wt. %, from about 0.5 wt. % to about 3 wt. %, from about 0.5 wt. % to about 2 wt. %, from about 0.5 wt. % to about 1 wt. %, from about 1 wt. % to about 3 wt. %, or from about 1 wt. % to about 2 wt. % of the total chlorophenol content of the aqueous extract.

The chlorophenol feed mixture can further comprise 3,4-dichlorophenol. The pKa of 3,4-dichlorophenol is 8.69, which is greater than that for 2,4-dichlorophenol. Thus, when present in the feed mixture, 3,4-dichlorophenol will generally partition in the organic extract along with 2,4-dichlorophenol. As such, the organic extract comprising 2,4-dichlorophenol in the organic phase can further comprise 3,4-dichlorophenol. To avoid an accumulation of 3,4-dichlorophenol in an integrated isomerization zone where the recycled chlorophenol feed mixture is used, it is necessary to remove 3,4-dichlorophenol. In various embodiments, as discussed further herein, 3,4-dichlorophenol can be substantially removed from the feed mixture prior to the FLLE zone. Therefore, in these and other embodiments, the organic extract comprising 2,4-dichlorophenol in the organic phase can be substantially free of 3,4-dichlorophenol.

The chlorophenol feed mixture can further comprise 2,3-dichlorophenol. The pKa of 2,3-dichlorophenol is 7.76 which is between that of 2,4-dichlorophenol and 2,5-dichlorophenol. Thus, when present in the feed mixture, 2,3-dichlorophenol will generally be present in both the aqueous extract along with 2,5-dichlorophenol and the organic extract along with 2,4-dichlorophenol. As such, the aqueous extract comprising 2,5-dichlorophenol and/or a salt thereof in the aqueous phase can further comprise 2,3-dichlorophenol and/or a salt thereof and the organic extract comprising 2,4-dichlorophenol in the organic phase can further comprise 2,3-dichlorophenol as well. Also, the aqueous extract and organic extract can contain comparable amounts of total 2,3-dichlorophenol. Accordingly, in various embodiments, total 2,3-dichlorophenol can constitute no more than about 1 wt. %, no more than about 0.5 wt. %, or no more than about 0.1 wt. % of the total chlorophenol content of the aqueous extract and/or the organic extract. For example, total 2,3-dichlorophenol can constitute from about 0.1 wt. % to about 1 wt. %, or from about 0.1 wt. % to about 0.5 wt. % of the total chlorophenol content of the aqueous extract and/or the organic extract.

The chlorophenol feed mixture can further comprise various monochlorophenols. The pKas of 2-monochlorophenol, 3-monochlorophenol, and 4-monochlorophenol are 8.29, 8.79, and 9.14, respectively, which are greater than that for 2,4-dichlorophenol. Thus, when present in the feed mixture, monochlorophenols will generally partition in the organic extract along with 2,4-dichlorophenol. As such, the organic extract comprising 2,4-dichlorophenol in the organic phase can further comprise 2-monochlorophenol, 3-monochlorophenol, and/or 4-monochlorophenol.

As noted above, the chlorophenol feed mixture from phenol chlorination processes can further comprise 2,4,6-trichlorophenol. The pKa of 2,4,6-trichlorophenol is 6.21, which is less than that for 2,5-dichlorophenol. Thus, when present in the feed mixture, 2,4,6-trichlorophenol will generally partition in the aqueous extract along with 2,5-dichlorophenol. As such, the organic extract comprising 2,4-dichlorophenol in the organic phase can be substantially free of 2,4,6-trichlorophenol.

In some embodiments, the chlorophenol feed mixture can be substantially free of 2,5-dichlorophenol. For example, the chlorophenol feed mixture from phenol chlorination processes can comprise 2,4-dichlorophenol, 2- and/or 4-monochlorophenol, 2,6-dichlorophenol, and 2,4,6-trichlorophenol. In these embodiments, processes of the present invention can provide an organic extract that is enriched in 2,4-dichlorophenol. Accordingly, the organic extract comprising 2,4-dichlorophenol in the organic phase can be substantially free of 2,6-dichlorophenol and/or 2,4,6-trichlorophenol.

The FLLE zone is typically operated at ambient temperature and pressure conditions. Accordingly, the FLLE zone can be operated at a temperature of from about 15° C. to about 50° C.

Removal of 3,4-Dichlorophenol and 2,6-Dichlorophenol

The processes of the present invention can include various operations upstream of the FLLE zone, such as an operation for separating at least a portion of 3,4-dichlorophenol and 2,6-dichlorophenol (when present) from the feed mixture. Accordingly, processes of the present invention can further comprise feeding a crude chlorophenol feed mixture comprising 2,4-dichlorophenol; 2,5-dichlorophenol; 2,6-dichlorophenol; and 3,4-dichlorophenol to a dichlorophenol separation zone to separate at least a portion of the 2,4-dichlorophenol and 2,5-dichlorophenol from the 2,6-dichlorophenol and 3,4-dichlorophenol to form the chlorophenol feed mixture and a mixture comprising 2,6-dichlorophenol and 3,4-dichlorophenol. In various embodiments, the crude chlorophenol feed mixture separation zone comprises distilling the crude chlorophenol feed mixture.

Figure 2:
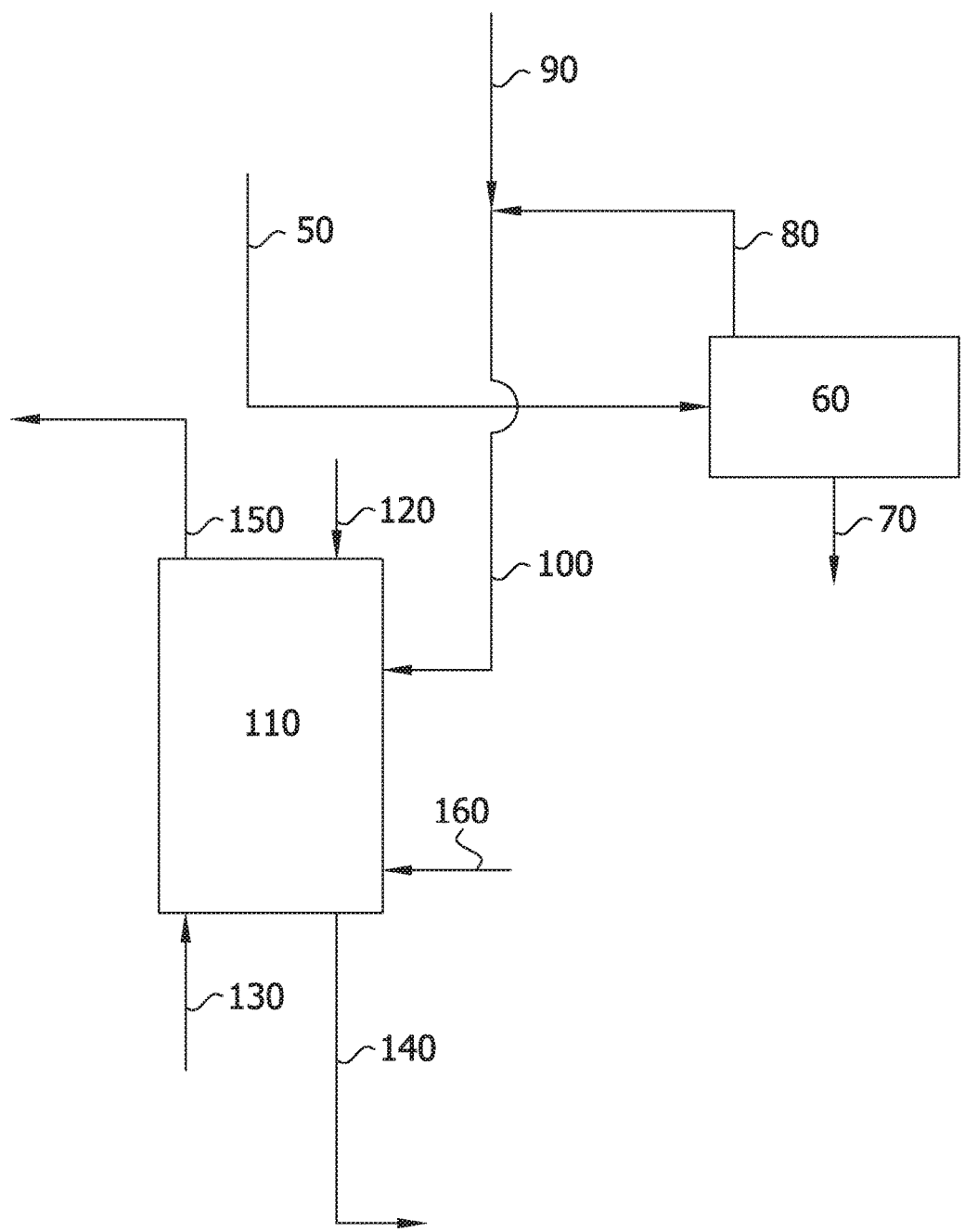
FIG. 2 presents a block flow diagram of a separation process including an upstream separation zone in accordance with various aspects of the present invention.

A block flow diagram illustrating a process including an upstream separation zone in accordance with various embodiments of the present invention is provided in FIG. 2. A crude chlorophenol feed mixture 50 containing various chlorophenols such as 2,4-dichlorophenol; 2,5-dichlorophenol; 2,6-dichlorophenol; and 3,4-dichlorophenol is introduced to dichlorophenol separation zone 60. The crude chlorophenol feed mixture can be obtained, for example, from an isomerization process (not shown) where a portion of 2,4-dichlorophenol is isomerized to 2,5-dichlorophenol. As noted, the separation zone can be a distillation zone. The normal boiling points of 2,6-dichlorophenol and 3,4-dichlorophenol are approximately 220° C. and 247° C., respectively, which are greater than the normal boiling points of 2,4-dichlorophenol (normal b.p. 209° C. to 210° C.) and 2,5-dichlorophenol (normal b.p. 211° C.). Thus, in a distillation operation it is possible to remove a significant fraction of 2,6-dichlorophenol and 3,4-dichlorophenol in bottoms stream 70 while the primary fraction of lower boiling chlorophenols including 2,4-dichlorophenol and 2,5-dichlorophenol is removed in the distillate (overhead product) stream 80 to form the chlorophenol feed mixture 100 to the FLLE zone. This stream is then fed to the FLLE zone 110 and the process proceeds as described above with respect to FIG. 1.

Typically, the mixture comprising 2,6-dichlorophenol and 3,4-dichlorophenol exiting the chlorophenol feed mixture separation zone comprises at least about 70 wt. %, at least about 75 wt. %, at least about 80 wt. %, at least about 85 wt. %, or at least about 90 wt. % of the 2,6-dichlorophenol content of the crude chlorophenol feed mixture. The mixture comprising 2,6-dichlorophenol and 3,4-dichlorophenol exiting the crude chlorophenol feed mixture separation zone can comprise at least about 80 wt. %, at least about 85 wt. %, at least about 90 wt. %, at least about 95 wt. %, or at least about 99 wt. % of the 3,4-dichlorophenol content of the crude chlorophenol feed mixture.

Referring to FIG. 2, the distillate stream 80 forming the chlorophenol feed mixture to the FLLE zone can optionally be combined with stream 90 comprising salts of 2,4-dichlorophenol and 2,5-dichlorophenol. 2,4-Dichlorophenol and 2,5-dichlorophenol can be recovered from effluent gases of an isomerization reactor that converts 2,4-dichlorophenol to 2,5-dichlorophenol. Scrubbing reactor effluent gases with a solution containing a base such as potassium hydroxide yields salts of 2,4-dichlorophenol and 2,5-dichlorophenol. These salts can then be separated in the FLLE zone.

Further Processing of Aqueous Extract Comprising 2,5-Dichlorophenol

The processes of the present invention can also include various operations downstream of the FLLE zone including further processing of the aqueous extract comprising 2,5-dichlorophenol and/or a salt thereof. Accordingly, processes of the present invention can further comprise feeding the aqueous extract comprising 2,5-dichlorophenol and/or a salt thereof in the aqueous phase to a water stripping zone to separate a portion of the water from 2,5-dichlorophenol and/or a salt thereof to form a concentrated extract comprising 2,5-dichlorophenol and/or a salt thereof.

Figure 3:
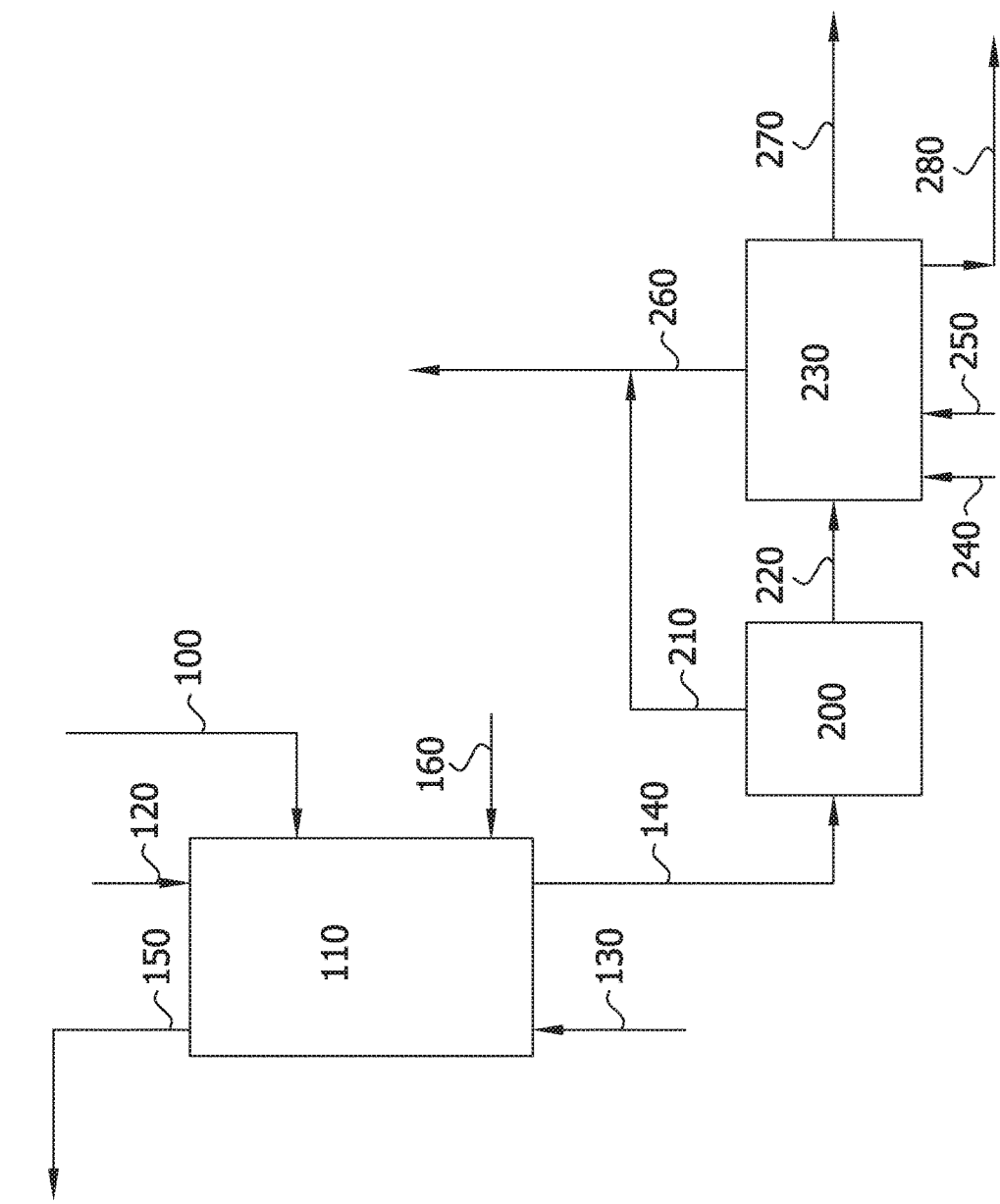
FIG. 3 presents a block flow diagram of a separation process including a downstream operation for further purifying the aqueous extract comprising 2,5-dichlorophenol and/or a salt thereof in accordance with various aspects of the present invention.

A block flow diagram illustrating a process including a downstream operation for further processing the aqueous extract comprising 2,5-dichlorophenol and/or a salt thereof in accordance with various embodiments of the present invention is provided in FIG. 3. A chlorophenol feed mixture 100 is introduced to FLLE zone 110 and the process proceeds as described above with respect to FIG. 1. The aqueous extract 140 comprising 2,5-dichlorophenol and/or a salt thereof in the aqueous phase exiting the FLLE zone 110 is fed to water stripping zone 200, such as a flash separator, where a portion of the water is removed from the extract in overhead stream 210. Typically, the water stripping zone reduces the water content of the extract comprising 2,5-dichlorophenol and/or a salt thereof to from about 80 to 90 wt. % when the water content of the extract is greater than 90 wt. % (e.g., between 92 and 95 wt. %). The concentrated extract 220 comprising 2,5-dichlorophenol and/or a salt thereof, and having reduced water content exits the water stripping zone 200.

Overhead water stream 210 from the water stripping zone can be further treated in to remove residual chlorophenols. For example, the water can be purified using a carbon-bed (not shown on FIG. 3).

To further dehydrate the concentrated extract 220, it can then be introduced to a multi-stage crystallization zone 230. In the first stage of this zone, base 240 is added to the concentrated extract to form an aqueous solution comprising a salt of 2,5-dichlorophenol. The base can be the same as the base used in the FLLE zone (stream 120). For example, the base can be potassium hydroxide, which can be fed to the crystallization zone 230 as an aqueous solution. The pH of the fraction comprising a salt of 2,5-dichlorophenol can be controlled by the amount of base added. In various embodiments, the pH of the aqueous solution comprising a salt of 2,5-dichlorophenol is adjusted within the range of about 9.0 to about 9.2, and the molar ratio of the base to the 2,5-dichlorophenol in the concentrated extract is at least about 1:1.

Further, in the next stage of the crystallization zone 230, an organic solvent 250 can be mixed with the aqueous solution comprising a salt of 2,5-dichlorophenol. The organic solvent is an anti-solvent that forces the crystallization of the ionic salt comprising a cation of the base and an ion of the acid (e.g., potassium chloride). The organic solvent can be the same as the organic solvent used in the FLLE zone (e.g., xylenes). Heat is applied in this stage to remove water and a portion of the organic solvent in overhead stream 260. In this stage, the crystallization mixture is typically heated to a temperature of from about 140° C. to about 170° C. Removal of water yields a slurry comprising the salt of 2,5-dichlorophenol, the organic solvent, and the ionic salt solids. After hot crystallization of the ionic salt, the slurry comprising the salt of 2,5-dichlorophenol, the organic solvent, and the ionic salt can also be cooled (e.g., to a temperature of from about 40° C. to about 50° C.) to provide further time for the ionic salt crystallization. The solids fraction 280 comprising the ionic salt can then be separated from the concentrated liquid 270 comprising a salt of the 2,5-dichlorophenol and organic solvent by suitable solid-liquid separation techniques, for example centrifugation. The solids fraction can also be washed with organic solvent to remove residual 2,5-dichlorophenol from the solids. The wash can be recycled back to the hot crystallization stage of the crystallization zone 230 (not shown on FIG. 3). Typically, the concentrated liquid fraction comprising the salt of 2,5-dichlorophenol and the organic solvent has a concentration of the salt of the 2,5-dichlorophenol that is from about 15 wt. % to 25 wt. % or from about 15 wt. % to 20 wt. %.

The water and organic solvent removed in the hot crystallization stage can be introduced to a solvent recovery zone (not shown on FIG. 3) to recover a dehydrated organic solvent for recycling back to the hot crystallization stage of the crystallization zone. Overhead water stream 260 from the solvent recovery can be combined with overhead water stream 210 and recycled back for use in preparing the aqueous solution comprising base that is fed to the FLLE zone (not shown on FIG. 3).

Further Processing of Organic Extract Comprising 2,4-Dichlorophenol

Other operations downstream of the FLLE zone include further processing of the organic extract comprising 2,4-dichlorophenol. Accordingly, processes of the present invention can further comprise feeding the organic extract comprising 2,4-dichlorophenol in the organic phase to a 2,4-dichlorophenol recovery zone to separate the 2,4-dichlorophenol from the organic solvent to form a concentrated fraction comprising the 2,4-dichlorophenol and an organic fraction comprising the organic solvent.

Figure 4:
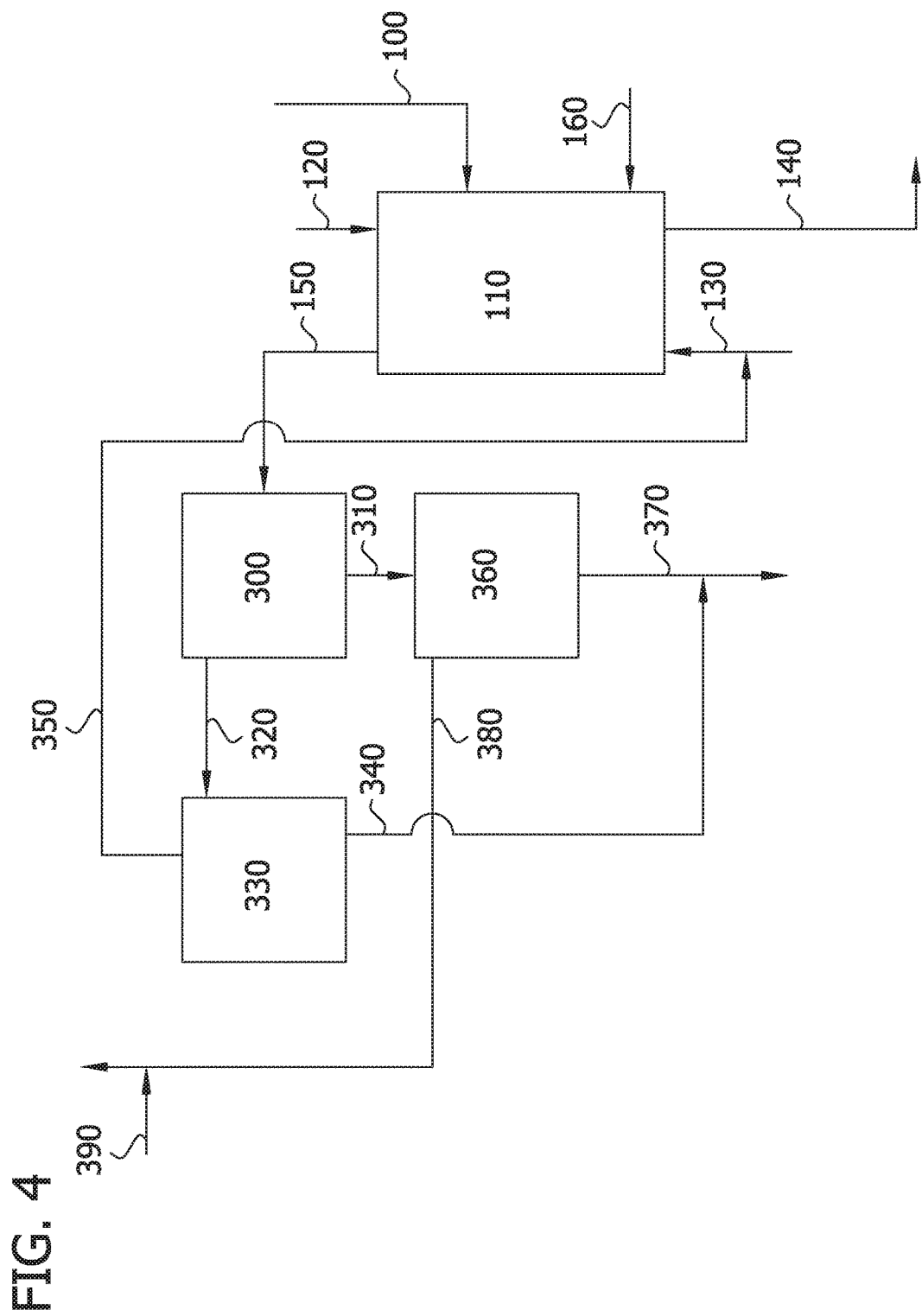
FIG. 4 presents a block flow diagram of a separation process including a downstream operation for further purifying the organic extract comprising 2,4-dichlorophenol in accordance with various aspects of the present invention.

A block flow diagram illustrating a process including a downstream operation for further processing the organic extract comprising 2,4-dichlorophenol in accordance with various embodiments of the present invention is provided in FIG. 4. A chlorophenol feed mixture 100 is introduced to FLLE zone 110 and the process proceeds as described above with respect to FIG. 1. The organic extract 150 comprising 2,4-dichlorophenol in the organic phase exiting the FLLE zone 110 is fed to 2,4-dichlorophenol recovery zone 300 to separate the 2,4-dichlorophenol from the organic solvent to form a concentrated fraction 310 comprising the 2,4-dichlorophenol and an organic fraction 320 comprising the organic solvent. The 2,4-dichlorophenol recovery zone can include distilling the organic extract comprising 2,4-dichlorophenol and the organic solvent.

As noted, the organic extract comprising 2,4-dichlorophenol in the organic phase can further comprise 2-monochlorophenol, 3-monochlorophenol, and/or 4-monochlorophenol. If present, 2-monochlorophenol will be removed with the organic solvent of the organic fraction in the 2,4-dichlorophenol recovery zone given its relatively low boiling point relative to 2,4-dichlorophenol, 3-monochlorophenol, and 4-monochlorophenol. Thus, the organic fraction comprising the organic solvent can further comprise 2-monochlorophenol.

Referring to FIG. 4, when 2-monochlorophenol is present in the organic fraction 320, the organic fraction can be further subjected to an organic solvent recovery zone 330 to separate 2-monochlorophenol from the organic fraction to form a fraction comprising 2-monochlorophenol 340 and a purified fraction 350 comprising the organic solvent. The organic solvent recovery zone can include distilling the organic fraction comprising the organic solvent and 2-monochlorophenol. Also, the purified fraction 350 comprising the organic solvent can be recycled back to the organic solvent stream 130 of the FLLE zone 110 or to organic solvent stream 250 of the crystallization zone 230 (recycle to stream 250 not shown) after cooling/condensing if necessary.

If present in the organic extract, 3-monochlorophenol and 4-monochlorophenol will be retained in the concentrated fraction 310 comprising 2,4-dichlorophenol exiting the 2,4-dichlorophenol recovery zone 300. As such, the concentrated fraction comprising 2,4-dichlorophenol can further comprise 3-monochlorophenol and/or 4-monochlorophenol.

Referring to FIG. 4, when 3-monochlorophenol (3-MCP) and 4-monochlorophenol (4-MCP) are present in the concentrated fraction 310, the concentrated fraction can be further subjected to a 3-MCP/4-MCP removal zone 360 to separate these species from 2,4-dichlorophenol to form a monochlorophenol fraction 370 comprising 3-monochlorophenol and 4-monochlorophenol and a purified fraction 380 comprising 2,4-dichlorophenol. The 3-MCP/4-MCP removal zone can comprise distilling the fraction comprising 2,4-dichlorophenol, 3-monochlorophenol, and 4-monochlorophenol.

In various embodiments, the purified fraction comprising the 2,4-dichlorophenol can be recycled back to an isomerization zone (not shown) to isomerize at least a portion of the 2,4-dichlorophenol to 2,5-dichlorophenol. Also, fresh feed 390 comprising 2,4-dichlorophenol can be mixed with the purified fraction comprising 2,4-dichlorophenol prior to or concomitantly with feeding into the isomerization zone.

The purified fraction comprising 2,4-dichlorophenol may further comprise 2,5-dichlorophenol. In these cases, the molar ratio of 2,5-dichlorophenol to 2,4-dichlorophenol is typically no more than about 1:5, about 1:10, about 1:25, or no more than about 1:50.

Further, the monochlorophenol streams 340 and 370 can be combined for further disposition. That is, the fraction comprising 3-monochlorophenol and 4-monochlorophenol from 3-MCP/4-MCP removal zone and the fraction comprising 2-monochlorophenol from the organic solvent recovery zone can be combined if desired.

As discussed further below, the organic extract comprising 2,4-dichlorophenol and/or the purified fraction comprising 2,4-dichlorophenol can also be fed to a process for producing 2,4-D (not shown).

Integrated Processes

Figure 5:
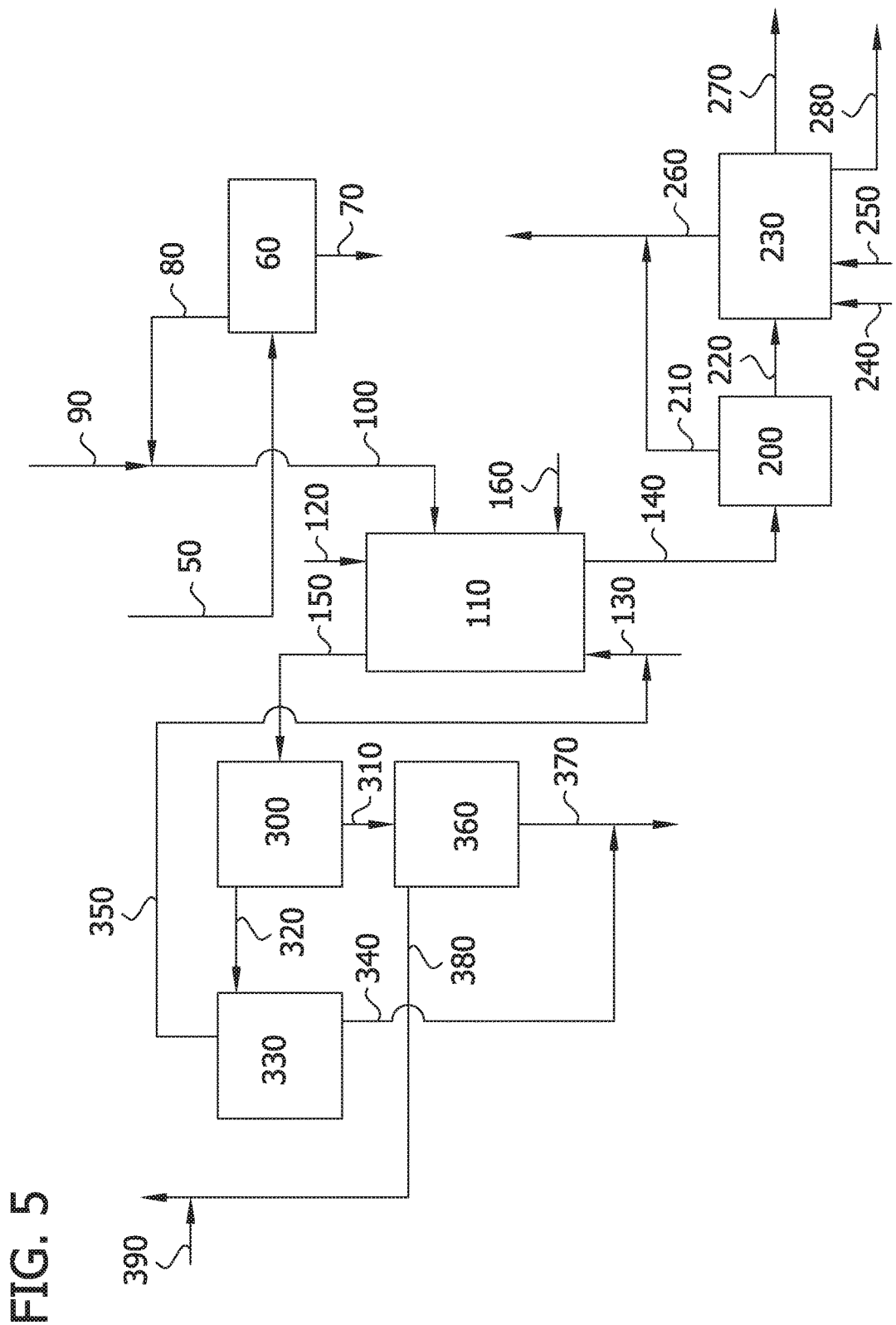
FIG. 5 presents a block flow diagram of an integrated process including the separation process and various upstream and downstream operations in accordance with various aspects of the present invention.

A block flow diagram illustrating an integrated process in accordance with various embodiments of the present invention is provided in FIG. 5. The integrated process proceeds as described above with respect to FIGS. 1 through 4.

Production of 3,6-Dichloro-2-Methoxybenzoic Acid (Dicamba) or Salt or Ester Thereof The 2,5-dichlorophenol and/or a salt thereof obtained from the aqueous extract removed from the FLLE zone can be further converted to 3,6-dichloro-2-methoxybenzoic acid (dicamba) or salt or ester thereof. In particular, various processes of the present invention further comprise carboxylating 2,5-dichlorophenol or salt or ester thereof obtained from the further processes of the aqueous extract removed from the FLLE zone to form 2-hydroxy-3,6-dichlorobenzoic acid or salt or ester thereof. The 2,5-dichlorophenol in the concentrated liquid 270 (refer to FIG. 3) is a suitable salt form for carboxylation. Therefore, processes of the present invention, described herein, may have an advantage over others known in the art by avoiding the further step of forming a salt of 2,5-dichlorophenol with a base during the carboxylation step. Subsequently, the 2-hydroxy-3,6-dichlorobenzoic acid or salt thereof is methylated with a methylating agent to form 3,6-dichloro-2-methoxybenzoic acid or salt thereof and/or methyl 3,6-dichloro-2-methyoxybenzoate. One example of a methylating agent includes dimethyl sulfate. See, for example U.S. Pat. No. 3,013,054, which is incorporated herein by reference. Further, methyl 3,6-dichloro-2-methyoxybenzoate can be saponified with a base to from a salt of 3,6-dichloro-2-methoxybenzoic acid. Acidification of the salt of 3,6-dichloro-2-methoxybenzoic acid (e.g., with HCl) yields 3,6-dichloro-2-methoxybenzoic acid (i.e., dicamba acid).

Production of 2,4-Dichlorophenoxyacetic Acid (2,4-D) or Salt or Ester Thereof

The organic extract comprising 2,4-dichlorophenol and/or the purified fraction comprising 2,4-dichlorophenol can be fed to a process for producing 2,4-D. Processes for preparing 2,4-D from 2,4-dichlorophenol include those described in U.S. Pat. Nos. 2,480,817 and 2,651,659. Accordingly, in various embodiments, the 2,4-dichlorophenol obtained from the organic extract removed from the FLLE zone can be further converted to 2,4-dichlorophenoxyacetic acid or salt or ester thereof.

Features described herein with respect to the processes of the present invention can be used either singularly or in combination.

Having described the invention in detail, it will be apparent that modifications and variations are possible without departing from the scope of the invention defined in the appended claims.

EXAMPLES

The following non-limiting examples are provided to further illustrate the present invention.

Example 1: Reverse-Phase High-Performance Liquid Chromatography ("RP-HPLC") Analytical Method for Determination of Chlorinated Phenols RP-HPLC analysis is used to monitor the compositions of chlorinated phenols in both organic phase and aqueous phase at the each stage of the fractional liquid-liquid extraction. The analysis was conducted on an Agilent 1260 Infinity Analytical HPLC System equipped with a diode array UV detector and monitored at 220 nm. The column was an X-Bridge C18, 4.6×150 mm, 3.5 micron with a pre-column filter and the column temperature was at 30° C. The HPLC was conducted at a flow rate of 2 mL/minute of mobile phase A (85% water, 15% acetonitrile) and mobile phase B (100% acetonitrile) as described in Tables 1-A and 1-B below:

TABLE 1-A

HPLC Method for Determination of Chlorinated Phenols

| TIME | % MPA | % MPB |
|---|---|---|
| 0.00 | 85 | 15 |
| 17.50 | 85 | 15 |
| 17.51 | 5 | 95 |
| 20.00 | 5 | 95 |
| 20.10 | 85 | 15 |
| 24.00 | 85 | 15 |

TABLE 1-B

Retention Times of Monochlorophenols and Dichlorophenols by Chlorinated Phenol Method

| Monochlorophenols | Retention Time (minute) | Dichlorophenols | Retention Time (minute) |
|---|---|---|---|
| 2-Chlorophenol | 4.89 | 2,6-Dichlorophenol | 9.54 |
| 4-Chlorophenol | 6.13 | 2,3-Dichlorophenol | 12.12 |
| 3-Chlorophenol | 6.56 | 2,5-Dichlorophenol | 13.45 |
|  |  | 2,4-Dichlorophenol | 14.50 |
|  |  | 3,4-Dichlorophenol | 15.71 |

Example 2: 15-Single Stage Fractional Liquid-Liquid Extraction System (Synthetic Feed)

A 15-single stage system of a fractional liquid-liquid extraction was used to demonstrate the separation of 2,4-dichlorophenol and 2,5-dichlorophenol from a chlorophenol feed mixture. The extraction apparatus included 15 single stage extraction vessels in series. A feed mixture containing various mono- and dichlorophenols in xylene was fed into the 15-single stage fractional liquid-liquid extraction system at stage 9. The composition of the feed mixture is presented in Table 1.

To start the experiment, portions of the feed mixture in xylenes and aqueous solutions of KOH were added to each of the 15 vessels. The initial amount of feed mixture (which also included other chlorophenol impurities) added to each of the vessels was 1/15th of the feed mixture entering in stage 9 (i.e., approximately 0.53 grams (8 grams of feed mixture is added in stage 9).

Figure 6:
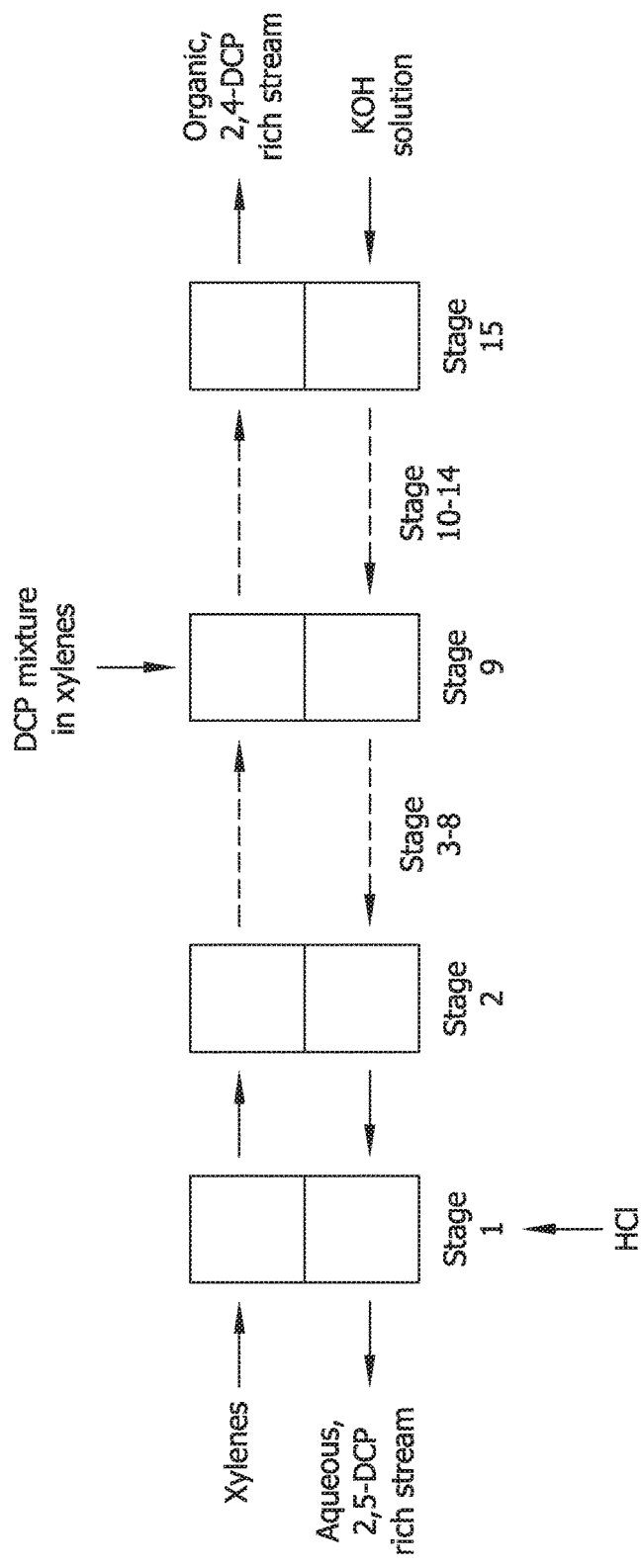
FIG. 6 presents a diagram of the bench-top 15-stage counter current extraction process described in Example 2.

During steady state operation, fresh organic solvent (xylenes) was introduced at stage 1 and fresh aqueous KOH solution (3-5 wt. %) was introduced at stage 15. The organic stream and the aqueous stream moved in a counter-current direction with respect to each other. As demonstrated in FIG. 6, the organic stream moved from stage 1 to stage 2 and from stage 2 to stage 3 and so forth, whereas the aqueous stream moved from stage 15 to stage 14, from stage 14 to stage 13 and so forth. The amount of aqueous KOH solution, added at stage 15, was determined by the amount of 2,5-dichlorophenol in the feed and the molar ratio of KOH to 2,5-dichlorophenol was maintained at approximately 2.75. The aqueous HCl solution (20 wt. %) was fed at stage 1 to adjust the pH of the aqueous stream. The amount of aqueous HCl solution was determined by the amount of aqueous KOH solution and the molar ratio of HCl to KOH was maintained at approximately 0.8. The synthetic dichlorophenol feed was dissolved in xylenes and was then added to stage 9. The organic and aqueous phases at each stage were shaken for about one minute, and then allowed to sit for about 6 minutes before separating the two phases. At steady state, the compositions of chlorophenols in both aqueous and organic phases of each stage were analyzed by the RP-HPLC analytical method and the corresponding pH value of the aqueous phase was measured. The results are presented in Table 3-A and Table 3-B.

TABLE 2-A

Composition of Chlorophenols in the Aqueous Phase and pH Values

| Stage | 2-CP (wt. %) | 4-CP (wt. %) | 3-CP (wt. %) | 2,6-DCP (wt. %) | 2,3-DCP (wt. %) | 2,5-DCP (wt. %) | 2,4-DCP (wt. %) | 3,4-DCP (wt. %) | pH |
|---|---|---|---|---|---|---|---|---|---|
| Feed Mixture | 0.004 | 0.56 | 0.35 | 0.20 | 0.23 | 31.85 | 66.00 | 0.82 | — |
| 1 | 0.001 | 0.00 | 0.00 | 1.09 | 0.28 | 97.49 | 1.14 | 0.00 | 8.79 |
| 2 | 0.002 | 0.00 | 0.00 | 0.51 | 0.38 | 96.42 | 2.69 | 0.00 | 9.85 |
| 3 | 0.003 | 0.00 | 0.01 | 0.31 | 0.37 | 95.44 | 3.87 | 0.00 | 9.86 |
| 4 | 0.005 | 0.00 | 0.01 | 0.31 | 0.43 | 92.28 | 6.95 | 0.00 | 9.78 |
| 5 | 0.007 | 0.01 | 0.02 | 0.35 | 0.51 | 87.60 | 11.48 | 0.00 | 9.78 |
| 6 | 0.010 | 0.03 | 0.05 | 0.33 | 0.49 | 81.85 | 17.23 | 0.00 | 9.76 |
| 7 | 0.013 | 0.05 | 0.08 | 0.31 | 0.46 | 75.96 | 23.04 | 0.05 | 9.80 |
| 8 | 0.013 | 0.12 | 0.13 | 0.32 | 0.44 | 66.61 | 32.30 | 0.00 | 9.74 |
| 9 | 0.015 | 0.24 | 0.20 | 0.30 | 0.38 | 59.31 | 39.25 | 0.19 | 9.60 |
| 10 | 0.015 | 0.24 | 0.20 | 0.11 | 0.41 | 56.97 | 41.93 | 0.00 | 9.66 |
| 11 | 0.017 | 0.24 | 0.20 | 0.04 | 0.42 | 55.99 | 42.65 | 0.32 | 9.71 |
| 12 | 0.017 | 0.27 | 0.23 | 0.01 | 0.44 | 49.41 | 49.26 | 0.22 | 9.72 |
| 13 | 0.017 | 0.27 | 0.23 | 0.01 | 0.44 | 44.36 | 54.18 | 0.37 | 9.74 |
| 14 | 0.017 | 0.31 | 0.28 | 0.00 | 0.41 | 33.55 | 64.81 | 0.46 | 9.76 |
| 15 | 0.017 | 0.34 | 0.30 | 0.00 | 0.33 | 23.33 | 75.03 | 0.48 | 9.94 |

Each chlorophenolate in the aqueous phase was fully neutralized to chlorophenol during the RP-HPLC analysis as a part of the reported chlorophenol content.

TABLE 2-B

Composition of Chlorophenols in the Organic Phase

| | 2-CP (wt. %) | 4-CP (wt. %) | 3-CP (wt. %) | 2,6-DCP (wt. %) | 2,3-DCP (wt. %) | 2,5-DCP (wt. %) | 2,4-DCP (wt. %) | 3,4-DCP (wt. %) |
|---|---|---|---|---|---|---|---|---|
| Feed Mixture Stage | 0.004 | 0.56 | 0.35 | 0.20 | 0.23 | 31.85 | 66.00 | 0.82 |
| 1 | 0.003 | 0.00 | 0.00 | 0.27 | 0.38 | 96.32 | 3.02 | 0.00 |
| 2 | 0.004 | 0.00 | 0.01 | 0.11 | 0.42 | 94.50 | 4.95 | 0.00 |
| 3 | 0.005 | 0.00 | 0.01 | 0.03 | 0.48 | 91.16 | 8.30 | 0.00 |
| 4 | 0.011 | 0.02 | 0.04 | 0.02 | 0.59 | 83.03 | 16.30 | 0.00 |
| 5 | 0.010 | 0.03 | 0.05 | 0.03 | 0.53 | 78.84 | 20.53 | 0.00 |
| 6 | 0.013 | 0.06 | 0.09 | 0.02 | 0.47 | 66.88 | 32.45 | 0.00 |
| 7 | 0.020 | 0.15 | 0.17 | 0.01 | 0.50 | 58.42 | 40.63 | 0.10 |
| 8 | 0.014 | 0.27 | 0.22 | 0.05 | 0.35 | 47.09 | 52.01 | 0.00 |
| 9 | 0.008 | 0.51 | 0.35 | 0.05 | 0.35 | 39.75 | 58.36 | 0.63 |
| 10 | 0.015 | 0.48 | 0.37 | 0.00 | 0.34 | 37.45 | 60.81 | 0.54 |
| 11 | 0.018 | 0.48 | 0.37 | 0.00 | 0.36 | 36.66 | 61.56 | 0.55 |
| 12 | 0.006 | 0.53 | 0.38 | 0.00 | 0.36 | 30.38 | 67.82 | 0.53 |
| 13 | 0.018 | 0.57 | 0.45 | 0.00 | 0.37 | 25.10 | 72.84 | 0.65 |
| 14 | 0.016 | 0.59 | 0.47 | 0.00 | 0.15 | 14.87 | 83.07 | 0.82 |
| 15 | 0.025 | 0.90 | 0.57 | 0.00 | 0.25 | 13.85 | 83.23 | 1.17 |

Comparing the exiting organic phase of stage 15 to the aqueous phase of stage 1, the chlorophenols with pKa values of 8.0 or greater (i.e. monochlorophenols, 3,4-dichlorophenol, and 2,4-dichlorophenol) were recovered in the organic phase of stage 15 while being essentially absent in the aqueous phase of stage 1. The concentration of these molecules increased with the increase of stage number in both aqueous and organic phases. The 2,3-dichlorophenol has a pKa of 7.76, which is between the pKa of 2,4-dichlorophenol (8.09) and the pKa of 2,5-dichlorophenol (7.51). As a result, the 2,3-dichlorophenol was recovered in both phases. Except for the 2,5-dichlorophenol, the other mono- and di-chlorophenols are preferred in the organic phase. The purity of 2,5-dichlorophenol and/or potassium salt of 2,5-dichlorophenol was enhanced at the exiting stream of stage 1, as demonstrated in this 15-single stage fractional liquid-liquid extraction system. Due to pKa (6.79) of the 2,6-dichlorophenol, this impurity stays in the 2,5-dichlorophenol enriched aqueous stream if the feed contains the 2,6-dichlorophenol.

Example 3: 15-Single Stage Fractional Liquid-Liquid Extraction System (Feed from Isomerization Reactor)

Example 2 was repeated with the mixture from the isomerization reaction of 2,4-dichlorophenol to 2,5-dichlorophenol using a calcined HZSM-5 zeolite. Similar separation results were observed compare to the synthetic mixture. The mono-chlorophenols, 3,4-dichlorophenol and 2,4-dichlorophenol were selectively retained in the organic phase of stage 15, while 2,5-dichlorophenol and 2,6-dichlorophenol were extracted to the aqueous phase of stage 1. The results are presented in Table 4-A and Table 4-B.

TABLE 3-A

Composition of Chlorophenols in the Aqueous Phase of Stage 1 and the Organic Phase of Stage 15

| | 2-CP (wt. %) | 4-CP (wt. %) | 3-CP (wt. %) | 2,6-DCP (wt. %) | 2,3-DCP (wt. %) | 2,5-DCP (wt. %) | 2,4-DCP (wt. %) | 3,4-DCP (wt. %) | pH |
|---|---|---|---|---|---|---|---|---|---|
| Synthetic feed | 0.004 | 0.56 | 0.35 | 0.20 | 0.23 | 31.85 | 66.00 | 0.82 | — |
| Aqueous phase of Stage 1 | 0.001 | 0.00 | 0.00 | 1.09 | 0.28 | 97.49 | 1.14 | 0.00 | 8.79 |
| Organic phase of Stage 15 | 0.025 | 0.90 | 0.57 | 0.00 | 0.25 | 13.85 | 83.23 | 1.17 | — |
| Feed obtained from isomerization reactor | 0.43 | 0.67 | 1.20 | 0.47 | 0.14 | 22.55 | 73.59 | 0.95 | — |
| Aqueous phase of Stage 1 | 0.13 | 0.00 | 0.01 | 2.58 | 0.34 | 91.87 | 5.04 | 0.03 | 8.33 |
| Organic phase of Stage 15 | 0.44 | 0.86 | 1.52 | 0.01 | 0.13 | 9.88 | 86.11 | 1.05 | — |

Each chlorophenolate in the aqueous phase was fully neutralized to chlorophenol during the RP-HPLC analysis as a part of the reported chlorophenol content.

TABLE 3-B

Recovery of Chlorophenols in the Aqueous Phase
of Stage 1 and the Organic Phase of Stage 15

|  | 2-CP | 4-CP | 3-CP | 2,6-DCP | 2,3-DCP | 2,5-DCP | 2,4-DCP | 3,4-DCP | pH |
|---|---|---|---|---|---|---|---|---|---|
| Synthetic feed (mg) | 0.3 | 41.8 | 26.6 | 15.3 | 17.6 | 2395.1 | 4960.7 | 61.6 | — |
| Aqueous phase of Stage 1 (Recovery %) | 0.0% | 0.0% | 0.0% | 100% | 27% | 71% | 0.5% | 0.0% | 8.79 |
| Organic phase of Stage 15 (Recovery %) | 100% | 100% | 100% | 0.0% | 73% | 29% | 99% | 100% | — |
| Feed obtained from isomerization reactor (mg) | 33.8 | 52.1 | 93.8 | 37.0 | 10.6 | 1761.9 | 5749.1 | 74.4 | — |
| Aqueous phase of Stage 1 (Recovery %) | 6% | 0.0% | 0.2% | 99% | 37% | 67% | 1.2% | 0.8% | 8.33 |
| Organic phase of Stage 15 (Recovery %) | 94% | 100% | 100% | 1.1% | 63% | 33% | 99% | 99% |  |

Each chlorophenolate in the aqueous phase was fully neutralized to chlorophenol during the RP-HPLC analysis as a part of the reported chlorophenol content.

Embodiments

For further illustration, additional non-limiting embodiments of the present disclosure are set forth below.

For example, embodiment 1 is a process for producing an aqueous extract comprising 2,5-dichlorophenol and/or a salt thereof, the process comprising:

feeding a chlorophenol feed mixture comprising 2,5-diclorophenol and 2,4-dichlorophenol to a fractional liquid-liquid extraction (FLLE) zone comprising a rectifying section and a stripping section;

feeding an organic solvent to the stripping section of the FLLE zone;

feeding an aqueous solution comprising base to the rectifying section of the FLLE zone;

contacting the feed mixture with the organic solvent and the aqueous solution in the FLLE zone, wherein at least a portion of the 2,5-diclorophenol is transferred to an aqueous phase comprising the aqueous solution and at least a portion of the 2,4-dichlorophenol is transferred to an organic phase comprising the organic solvent;

removing the aqueous extract comprising 2,5-dichlorophenol and/or a salt thereof in the aqueous phase from the stripping section of the FLLE zone, wherein the weight ratio of total 2,5-dichlorophenol to total 2,4-dichlorophenol in the aqueous extract is greater than the weight ratio of 2,5-dichlorophenol to 2,4-dichlorophenol in the chlorophenol feed mixture; and removing an organic extract comprising 2,4-dichlorophenol in the organic phase from the rectifying section of the FLLE zone.

Embodiment 2 is the process of embodiment 1 wherein the rectifying section comprises a series of stages.

Embodiment 3 is the process of embodiment 1 or 2 wherein the stripping section comprises a series of stages.

Embodiment 4 is the process of any one of embodiments 1 to 3 wherein the FLLE zone comprises at least one vertical column having a feed location for the chlorophenol feed mixture and wherein the rectifying section is the portion of the column situated above the feed location and the stripping section is the portion of the column situated beneath the feed location.

Embodiment 5 is the process of any one of embodiments 1 to 4 wherein the organic solvent is fed into a stage that is positioned within a lower portion of the stripping section.

Embodiment 6 is the process of any one of embodiments 1 to 5 wherein the organic solvent comprises an aromatic solvent.

Embodiment 7 is the process of embodiment 6 wherein the aromatic solvent is selected from the group consisting of benzene, toluene, xylenes, and mixtures thereof.

Embodiment 8 is the process of any one of embodiments 1 to 7 wherein the organic solvent comprises xylenes.

Embodiment 9 is the process of any one of embodiments 1 to 8 wherein the organic solvent comprises an alkyl, dialkyl ether, or halogenated alkyl solvent.

Embodiment 10 is the process of embodiment 9 wherein the alkyl solvent is selected from the group consisting of hexane, heptane, octane, and mixtures thereof.

Embodiment 11 is the process of embodiment 9 or 10 wherein the dialkyl ether solvent has a general formula of R—O—R', wherein R and R' are each independently a $C_1$-$C_6$ alkyl.

Embodiment 12 is the process of any one of embodiments 9 to 11 wherein the dialkyl ether solvent is selected from the group consisting of methyl butyl ether, dibutyl ether, cyclopentyl methyl ether, and mixtures thereof.

Embodiment 13 is the process of any one of embodiments 1 to 12 wherein the weight ratio of organic solvent to the chlorophenol feed mixture fed to the FLLE zone is from about 1:1 to about 15:1, from about 2:1 to about 10:1, from about 3:1 to about 10:1, or from about 3:1 to about 7:1.

Embodiment 14 is the process of any one of embodiments 1 to 13 wherein the aqueous solution comprising base is fed into a stage that is positioned within an upper portion of the rectifying section.

Embodiment 15 is the process of any one of embodiments 1 to 14 wherein the base comprises an alkali or alkaline earth hydroxide, carbonate, or bicarbonate.

Embodiment 16 is the process of any one of embodiments 1 to 15 wherein the base comprises potassium hydroxide.

Embodiment 17 is the process of embodiment 16 wherein the concentration of potassium hydroxide in the aqueous solution comprising base that is fed to the FLLE zone is from about 1 wt. % to about 10 wt. %, from about 2 wt. % to about 7 wt. %, from about 3 wt. % to about 7 wt. %, from about 3 wt. % to about 5 wt. %, or from about 2 wt. % to about 5 wt. %.

Embodiment 18 is the process of any one of embodiments 1 to 17 wherein the molar ratio of the base to 2,5-dichlorophenol in the chlorophenol feed mixture is from about 0.5:1 to about 5:1, from about 0.5:1 to about 3:1, from about 0.9:1 to about 3:1, from about 1.5:1 to about 3:1, or from about 2:1 to about 3:1.

Embodiment 19 is the process of any one of embodiments 1 to 18 further comprising feeding an aqueous solution comprising acid to the stripping section of the FLLE zone.

Embodiment 20 is the process of embodiment 19 wherein the aqueous solution comprising acid is fed into a stage that is positioned within a lower portion of the stripping section in the FLLE zone.

Embodiment 21 is the process of embodiment 20 wherein the aqueous solution comprising acid is fed into a stage that is positioned in the lower 5% to 25%, 10% to 25%, or 10% to 20% of the stripping section.

Embodiment 22 is the process of any one of embodiments 19 to 21 wherein the acid is a mineral acid or an organic acid.

Embodiment 23 is the process of embodiment 22 wherein the mineral acid is selected from the group consisting of hydrochloric acid, sulfuric acid, and phosphoric acid.

Embodiment 24 is the process of embodiment 22 wherein the organic acid is selected from the group consisting of formic acid, acetic acid, propionic acid, butyric acid, citric acid and mixtures thereof.

Embodiment 25 is the process of any one of embodiments 19 to 21 wherein the acid comprises hydrochloric acid.

Embodiment 26 is the process of embodiment 25 wherein the concentration of hydrochloric acid in the aqueous solution that is fed to the FLLE zone is from about 5 wt. % to about 30 wt. %, from about 10 wt. % to about 30 wt. %, from about 15 wt. % to about 30 wt. %, from about 20 wt. % to about 30 wt. %, from about 25 wt. % to about 30 wt. %, from about 10 wt. % to about 25 wt. %, from about 15 wt. % to about 25 wt. %, or from about 20 wt. % to about 25 wt. %.

Embodiment 27 is the process of any one of embodiments 19 to 26 wherein the molar ratio of acid to base is from about 0.5:1 to about 2:1, from about 0.5:1 to about 1:1, or from about 0.6:1 to about 0.8:1.

Embodiment 28 is the process of any one of embodiments 1 to 27 wherein the pH of the aqueous extract comprising 2,5-dichlorophenol and/or a salt thereof in the aqueous phase exiting the stripping section is maintained between about 8 and about 9, between about 8.2 and about 8.8, or between about 8.4 and about 8.8.

Embodiment 29 is the process of any one of embodiments 1 to 28 wherein the pH of the aqueous phase contacting the organic extract comprising 2,4-dichlorophenol in the organic phase exiting the rectifying section is greater than the pH of the aqueous extract comprising 2,5-dichlorophenol and/or a salt thereof in the aqueous phase exiting the stripping section.

Embodiment 30 is the process of any one of embodiments 1 to 29 wherein the pH of the aqueous phase contacting the organic extract comprising 2,4-dichlorophenol in the organic phase exiting the rectifying section is between about 9 and about 10.5, between about 9.5 and about 10.5, or between about 9.5 and about 10.

Embodiment 31 is the process of any one of embodiments 1 to 30 wherein the weight ratio of 2,4-dichlorophenol to 2,5-dichlorophenol in the chlorophenol feed mixture to the FLLE zone is from about 1:1 to about 5:1, from about 1:1 to about 4:1, from about 1.5:1 to about 5:1, from about 2:1 to about 4:1, from about 2.5:1 to about 3.5:1, or about 3:1.

Embodiment 32 is the process of any one of embodiments 1 to 31 wherein the 2,5-dichlorophenol concentration in the chlorophenol feed mixture is at least about 5 wt. %, at least about 10 wt. %, at least about 20 wt. %, at least about 30 wt. %, at least about 40 wt. %, or at least about 50 wt. % of the total chlorophenol content.

Embodiment 33 is the process of any one of embodiments 1 to 31 wherein the 2,5-dichlorophenol concentration in the chlorophenol feed mixture is 5 wt. % to about 80 wt. %, from about 5 wt. % to about 70 wt. %, from about 5 wt. % to about 60 wt. %, from about 10 wt. % to about 80 wt. %, from about 10 wt. % to about 70 wt. %, from about 10 wt. % to about 60 wt. %, from about 20 wt. % to about 70 wt. %, from about 20 wt. % to about 60 wt. %, from about 30 wt. % to about 70 wt. %, from about 30 wt. % to about 60 wt. %, from about 40 wt. % to about 70 wt. %, or from about 40 wt. % to about 60 wt. % of the total chlorophenol content.

Embodiment 34 is the process of any one of embodiments 1 to 33 wherein the 2,4-dichlorophenol concentration in the chlorophenol feed mixture is at least about 5 wt. %, at least about 10 wt. %, at least about 20 wt. %, at least about 30 wt. %, at least about 40 wt. %, or at least about 50 wt. % of the total chlorophenol content.

Embodiment 35 is the process of any one of embodiments 1 to 33 wherein the 2,4-dichlorophenol concentration in the chlorophenol feed mixture is from about 10 wt. % to about 80 wt. %, from about 20 wt. % to about 80 wt. %, from about 30 wt. % to about 80 wt. %, from about 20 wt. % to about 50 wt. %, from about 30 wt. % to about 50 wt. %, from about 30 wt. % to about 40 wt. %, from about 35 wt. % to about 50 wt. %, or from about 35 wt. % to about 45 wt. % of the total chlorophenol content.

Embodiment 36 is the process of any one of embodiments 1 to 35 wherein the chlorophenol feed mixture further comprises salts of 2,4-dichlorophenol and 2,5-dichlorophenol.

Embodiment 37 is the process of embodiment 36 wherein the salts of 2,4-dichlorophenol and 2,5-dichlorophenol comprise potassium salts.

Embodiment 38 is the process of any one of embodiments 1 to 37 wherein the chlorophenol feed mixture further comprises 2-, 3-, and/or 4-monochlorophenol.

Embodiment 39 is the process of any one of embodiments 1 to 38 wherein the chlorophenol feed mixture further comprises 2,6-dichlorophenol.

Embodiment 40 is the process of any one of embodiments 1 to 39 wherein the chlorophenol feed mixture further comprises 3,4-dichlorophenol.

Embodiment 41 is the process of any one of embodiments 1 to 40 wherein the chlorophenol feed mixture further comprises 2,3-dichlorophenol.

Embodiment 42 is the process of any one of embodiments 1 to 41 wherein the total 2,5-dichlorophenol content in the aqueous extract is at least about 50 wt. %, at least about 60 wt. %, at least about 70 wt. %, at least about 80 wt. %, or at least about 90 wt. % of the total chlorophenol content in the aqueous extract.

Embodiment 43 is the process of any one of embodiments 1 to 41 wherein the total 2,5-dichlorophenol content in the aqueous extract is from about 55 wt. % to about 99 wt. %, from about 60 wt. % to about 99 wt. %, from about 70 wt. % to about 99 wt. %, from about 80 wt. % to about 99 wt. %, from about 90 wt. % to about 99 wt. %, from about 55 wt. % to about 90 wt. %, from about 60 wt. % to about 90 wt. %, from about 70 wt. % to about 90 wt. %, from about 65 wt. % to about 85 wt. %, or from about 70 wt. % to about 80 wt. % of the total chlorophenol content in the aqueous extract.

Embodiment 44 is the process of any one of embodiments 1 to 43 wherein the weight ratio of total 2,5-dichlorophenol to total 2,4-dichlorophenol in the aqueous extract is at least about 10:1 or at least about 15:1.

Embodiment 45 is the process of any one of embodiments 1 to 43 wherein the weight ratio of total 2,5-dichlorophenol to total 2,4-dichlorophenol in the aqueous extract is from about 10:1 to 200:1, from about 15:1 to about 200:1, from about 20:1 to about 200:1, from about 10:1 to about 100:1, from about 15:1 to about 100:1, or from about 20:1 to about 100:1.

Embodiment 46 is the process of any one of embodiments 1 to 45 wherein the aqueous extract comprising 2,5-dichlorophenol and/or a salt thereof in the aqueous phase further comprises 2,6-dichlorophenol and/or a salt thereof.

Embodiment 47 is the process of embodiment 46 wherein total 2,6-dichlorophenol constitutes no more than about 3 wt. %, no more than about 2 wt. %, no more than about 1 wt. %, or no more than about 0.5 wt. % of the total chlorophenol content in the aqueous extract.

Embodiment 48 is the process of embodiment 46 wherein total 2,6-dichlorophenol constitutes from about 0.1 wt. % to about 3 wt. %, from about 0.1 wt. % to 2 wt. %, from about 0.1 wt. % to about 1 wt. %, from about 0.1 wt. % to about 0.5 wt. %, from about 0.5 wt. % to about 3 wt. %, from about 0.5 wt. % to about 2 wt. %, from about 0.5 wt. % to about 1 wt. %, from about 1 wt. % to about 3 wt. %, or from about 1 wt. % to about 2 wt. % of the total chlorophenol content in the aqueous extract.

Embodiment 49 is the process of any one of embodiments 1 to 48 wherein the aqueous extract comprising 2,5-dichlorophenol and/or a salt thereof in the aqueous phase further comprises 2,3-dichlorophenol and/or a salt thereof.

Embodiment 50 is the process of embodiment 49 wherein total 2,3-dichlorophenol constitutes no more than about 1 wt. %, no more than about 0.5 wt. %, or no more than about 0.1 wt. % of the total chlorophenol content in the aqueous extract.

Embodiment 51 is the process of embodiment 49 wherein total 2,3-dichlorophenol constitutes from about 0.1 wt. % to about 1 wt. %, or from about 0.1 wt. % to about 0.5 wt. % of the total chlorophenol content in the aqueous extract.

Embodiment 52 is the process of any one of embodiments 1 to 51 wherein the 2,4-dichlorophenol content in the organic extract is at least about 50 wt. %, at least about 60 wt. %, at least about 70 wt. %, or at least about 80 wt. % of the total chlorophenol content in the organic extract.

Embodiment 53 is the process of any one of embodiments 1 to 51 wherein the 2,4-dichlorophenol content in the organic extract is from about 55 wt. % to about 95 wt. %, from about 60 wt. % to about 95 wt. %, from about 60 wt. % to about 90 wt. %, from about 70 wt. % to about 95 wt. %, from about 70 wt. % to about 90 wt. %, from about 70 wt. % to about 85 wt. %, from about 75 wt. % to about 95 wt. %, from about 75 wt. % to about 90 wt. %, or from about 80 wt. % to about 90 wt. % of the total chlorophenol content in the organic extract.

Embodiment 54 is the process of any one of embodiments 1 to 53 wherein the weight ratio of 2,4-dichlorophenol to 2,5-dichlorophenol in the organic extract is at least about 1.5:1, at least about 2:1, at least about 5:1, or at least 10:1.

Embodiment 55 is the process of any one of embodiments 1 to 53 wherein the weight ratio of 2,4-dichlorophenol to 2,5-dichlorophenol in the organic extract is from about 1.5:1 to about 100:1, from about 1.5:1 to about 50:1, from about 1.5:1 to about 20:1, from about 1.5:1 to about 10:1, from about 2:1 to about 100:1, from about 2:1 to about 50:1, from about 2:1 to about 20:1, from about 2:1 to about 10:1, from about 5:1 to about 100:1, from about 5:1 to about 50:1, from about 5:1 to about 20:1, from about 5:1 to about 10:1, from about 10:1 to about 100:1, from about 10:1 to about 50:1, or from about 10:1 to about 20:1.

Embodiment 56 is the process of any one of embodiments 1 to 55 wherein the organic extract comprising 2,4-dichlorophenol in the organic phase further comprises 2-monochlorophenol, 3-monochlorophenol, and 4-monochlorophenol.

Embodiment 57 is the process of any one of embodiments 1 to 56 wherein the organic extract comprising 2,4-dichlorophenol in the organic phase further comprises 2,3-dichlorophenol.

Embodiment 58 is the process of any one of embodiments 1 to 57 wherein the FLLE zone is operated at a temperature of from about 15° C. to about 50° C.

Embodiment 59 is the process of any one of embodiments 1 to 58 further comprising feeding a crude chlorophenol feed mixture comprising 2,4-dichlorophenol; 2,5-dichlorophenol; 2,6-dichlorophenol; and 3,4-dichlorophenol to a crude chlorophenol separation zone to separate at least a portion of the 2,4-dichlorophenol and 2,5-dichlorophenol from the 2,6-dichlorophenol and 3,4-dichlorophenol to form the chlorophenol feed mixture and a mixture comprising 2,6-dichlorophenol and 3,4-dichlorophenol.

Embodiment 60 is the process of embodiment 59 wherein the crude chlorophenol separation zone comprises distilling the crude chlorophenol feed mixture.

Embodiment 61 is the process of embodiments 59 and 60 wherein the mixture comprising 2,6-dichlorophenol and 3,4-dichlorophenol exiting the crude chlorophenol feed mixture separation zone comprises at least about 70 wt. %, at least about 75 wt. %, at least about 80 wt. %, at least about 85 wt. %, or at least about 90 wt. % of the 2,6-dichlorophenol content of the crude chlorophenol feed mixture.

Embodiment 62 is the process of any one of embodiments 59 to 61 wherein the mixture comprising 2,6-dichlorophenol and 3,4-dichlorophenol exiting the crude chlorophenol feed mixture separation zone comprises at least about 80 wt. %, at least about 85 wt. %, at least about 90 wt. %, at least about 95 wt. %, or at least about 99 wt. % of the 3,4-dichlorophenol content of the crude chlorophenol feed mixture.

Embodiment 63 is the process of any one of embodiments 59 to 62 wherein the crude chlorophenol feed mixture is obtained from an isomerization zone comprising isomerizing 2,4-dichlorophenol to 2,5-dichlorophenol.

Embodiment 64 is the process of any one of embodiments 1 to 63, further comprising feeding the organic extract comprising 2,4-dichlorophenol in the organic phase to a 2,4-dichlorophenol recovery zone to separate the 2,4-dichlorophenol from the organic phase to form a concentrated fraction comprising the 2,4-dichlorophenol and an organic fraction comprising the organic solvent.

Embodiment 65 is the process of embodiment 64 wherein the 2,4-dichlorophenol recovery zone comprises distilling the organic extract comprising 2,4-dichlorophenol in the organic phase.

Embodiment 66 is the process of embodiments 64 and 65 wherein the organic extract comprising 2,4-dichlorophenol in the organic phase further comprises 2-monochlorophenol, 3-monochlorophenol, and 4-monochlorophenol.

Embodiment 67 is the process of any one of embodiments 64 to 66 wherein the organic fraction comprising the organic solvent further comprises 2-monochlorophenol.

Embodiment 68 is the process of embodiment 67 further comprising separating 2-monochlorophenol from the organic fraction in an organic solvent recovery zone to form a fraction comprising 2-monochlorophenol and a purified fraction comprising the organic solvent.

Embodiment 69 is the process of embodiment 68 wherein the organic solvent recovery zone comprises distilling the organic fraction comprising 2-monochlorophenol and the organic solvent.

Embodiment 70 is the process of embodiment 68 or 69 further comprising recycling the purified fraction comprising the organic solvent back to the FLLE zone after any necessary cooling.

Embodiment 71 is the process of any one of embodiments 64 to 70 wherein the concentrated fraction comprising 2,4-dichlorophenol further comprises 3-monochlorophenol and 4-monochlorophenol.

Embodiment 72 is the process of embodiment 71 further comprising separating 3-monochlorophenol and 4-monochlorophenol from the 2,4-dichlorophenol in the concentrated fraction comprising 2,4-dichlorophenol, 3-monochlorophenol, and 4-monochlorophenol in a 3-MCP/4-MCP removal zone to form a monochlorophenol fraction comprising 3-monochlorophenol and 4-monochlorophenol and a purified fraction comprising 2,4-dichlorophenol.

Embodiment 73 is the process of embodiment 72 wherein the 3-MCP/4-MCP removal zone comprises distilling the fraction comprising 2,4-dichlorophenol, 3-monochlorophenol, and 4-monochlorophenol.

Embodiment 74 is the process of embodiment 72 or 73 further comprising recycling the purified fraction comprising the 2,4-dichlorophenol back to an isomerization zone to isomerize at least a portion of the 2,4-dichlorophenol to 2,5-dichlorophenol.

Embodiment 75 is the process of embodiment 74 further comprising mixing a fresh feed comprising 2,4-dichlorophenol with the purified fraction comprising 2,4-dichlorophenol prior to or concomitantly with feeding into the isomerization zone.

Embodiment 76 is the process of any one of embodiments 72 to 75 wherein the purified fraction comprising 2,4-dichlorophenol further comprises 2,5-dichlorophenol and the molar ratio of 2,5-dichlorophenol to 2,4-dichlorophenol is typically no more than about 1:5, about 1:10, about 1:25, or no more than about 1:50.

Embodiment 77 is the process of any one of embodiments 1 to 76 further comprising feeding the aqueous extract comprising 2,5-dichlorophenol and/or a salt thereof in the aqueous phase to a water stripping zone to separate a portion of the water from 2,5-dichlorophenol and/or a salt thereof to form a concentrated extract comprising 2,5-dichlorophenol and/or a salt thereof.

Embodiment 78 is the process of embodiment 77 wherein the concentrated extract comprising 2,5-dichlorophenol and/or a salt thereof has a water content from about 80 to 90 wt. %.

Embodiment 79 is the process of embodiment 77 or 78 further comprising adding a base to the concentrated extract comprising 2,5-dichlorophenol and/or a salt thereof in a first stage of a crystallization zone to form an aqueous solution comprising a salt of 2,5-dichlorophenol.

Embodiment 80 is the process of embodiment 79 wherein the base is the same as the base used in the FLLE zone.

Embodiment 81 is the process of embodiment 79 or 80 wherein the base is potassium hydroxide.

Embodiment 82 is the process of any one of embodiments 79 to 81 wherein the pH of the aqueous solution comprising a salt of 2,5-dichlorophenol is from 9.0 to 9.2, and the molar ratio of the base to the 2,5-dichlorophenol in the concentrated extract is about 1:1.

Embodiment 83 is the process of any one of embodiments 79 to 82 further comprising mixing an organic solvent with the aqueous solution comprising a salt of 2,5-dichlorophenol and crystallizing a solids fraction of an ionic salt comprising a cation of the base and an ion of the acid to form a crystallization mixture in a second stage of the crystallization zone.

Embodiment 84 is the process of embodiment 83 wherein the organic solvent used in the crystallization zone is the same as the organic solvent used in the FLLE zone.

Embodiment 85 is the process of embodiment 83 or 84 wherein the organic solvent comprises xylenes.

Embodiment 86 is the process of any one of embodiments 83 to 85 further comprising applying heat to the crystallization mixture to remove water and a portion of the organic solvent to form a slurry comprising the salt of 2,5-dichlorophenol, the organic solvent, and the ionic salt solids and a fraction comprising water and a portion of the organic solvent.

Embodiment 87 is the process of embodiment 86 wherein the crystallization mixture is heated to a temperature of from about 140° C. to about 170° C.

Embodiment 88 is the process of embodiment 86 or 87 further comprising cooling the slurry comprising the salt of 2,5-dichlorophenol, the organic solvent, and the ionic salt solids.

Embodiment 89 is the process of embodiment 88 wherein the slurry comprising the salt of 2,5-dichlorophenol, the organic solvent, and the ionic salt solids is cooled to a temperature of from about 40° C. to about 50° C.

Embodiment 90 is the process of any one of embodiments 86 to 89 further comprising separating the ionic salt solids from the salt of 2,5-dichlorophenol and the organic solvent to form a concentrated liquid fraction comprising the salt of 2,5-dichlorophenol and the organic solvent and a solids fraction comprising the ionic salt.

Embodiment 91 is the process of embodiment 90 wherein the separation comprises centrifuging the slurry comprising the salt of 2,5-dichlorophenol, the organic solvent, and the ionic salt solids.

Embodiment 92 is the process of embodiment 90 or 91 wherein the concentration of the salt of the 2,5-dichlorophenol in the concentrated liquid fraction is from about 15 wt. % to 25 wt. % or from about 15 wt. % to 20 wt. %.

Embodiment 93 is the process of embodiment 86 to 92 further comprising feeding the fraction comprising water and portion of the organic solvent removed from the crystallization mixture to a solvent recovery zone to recover a dehydrated organic solvent, and recycling the dehydrated organic solvent back to the crystallization zone.

Embodiment 94 is the process of any one of embodiments 77 to 93 further comprising purifying the water removed in the water stripping zone by removing residual chlorophenols.

Embodiment 95 is the process of embodiment 94 further comprising recycling the purified water and the water removed from the organic solvent in the solvent recovery zone back to the FLLE zone.

Embodiment 96 is the process of any one of embodiments 1 to 95 wherein at least a portion of the 2,5-dichlorophenol and/or a salt thereof obtained from the aqueous extract removed from the FLLE zone is further converted to 3,6-dichloro-2-methoxybenzoic acid or salt or ester thereof.

Embodiment 97 is the process of any one of embodiments 1 to 96, further comprising carboxylating 2,5-dichlorophenol or salt thereof obtained from the aqueous extract removed from the FLLE zone to form 2-hydroxy-3,6-dichlorobenzoic acid or salt thereof.

Embodiment 98 is the process of embodiment 97, further comprising methylating 2-hydroxy-3,6-dichlorobenzoic acid or salt thereof with a methylating agent to form 3,6-dichloro-2-methoxybenzoic acid or salt thereof and/or methyl 3,6-dichloro-2-methyoxybenzoate.

Embodiment 99 is the process of embodiment 98, further comprising saponifying methyl 3,6-dichloro-2-methyoxybenzoate with a base to from a salt of 3,6-dichloro-2-methoxybenzoic acid.

Embodiment 100 is a process for producing an organic extract comprising 2,4-dichlorophenol, the process comprising:

feeding a chlorophenol feed mixture comprising 2,4-diclorophenol and 2,5-dichlorophenol to a fractional liquid-liquid extraction (FLLE) zone comprising a rectifying section and a stripping section;

feeding an organic solvent to the stripping section of the FLLE zone;

feeding an aqueous solution comprising base to the rectifying section of the FLLE zone;

contacting the feed mixture with the organic solvent and the aqueous solution in the FLLE zone, wherein at least a portion of the 2,4-dichlorophenol is transferred to an organic phase comprising the organic solvent and at least a portion of the 2,5-diclorophenol is transferred to an aqueous phase comprising the aqueous solution;

removing the organic extract comprising 2,4-dichlorophenol in the organic phase from the rectifying section of the FLLE zone; and removing an aqueous extract comprising 2,5-dichlorophenol and/or a salt thereof in the aqueous phase from the stripping section of the FLLE zone, wherein the weight ratio of 2,4-dichlorophenol to 2,5-dichlorophenol in the organic extract is greater than the weight ratio of 2,4-dichlorophenol to 2,5-dichlorophenol in the chlorophenol feed mixture.

Embodiment 101 is the process of embodiment 100 wherein the chlorophenol feed is obtained from the reaction product of a process for the chlorination of phenol.

Embodiment 102 is the process of embodiment 100 or 101 wherein the rectifying section comprises a series of stages.

Embodiment 103 is the process of any one of embodiments 100 to 102 wherein the stripping section comprises a series of stages.

Embodiment 104 is the process of any one of embodiment 100 to 103 wherein the FLLE zone comprises at least one vertical column having a feed location for the chlorophenol feed mixture and wherein the rectifying section is the portion of the column situated above the feed location and the stripping section is the portion of the column situated beneath the feed location.

Embodiment 105 is the process of any one of embodiments 100 to 104 wherein the organic solvent is fed into a stage that is positioned within a lower portion of the stripping section.

Embodiment 106 is the process of any one of embodiments 100 to 105 wherein the organic solvent comprises an aromatic solvent.

Embodiment 107 is the process of embodiment 106 wherein the aromatic solvent is selected from the group consisting of benzene, toluene, xylenes, and mixtures thereof.

Embodiment 108 is the process of any one of embodiments 100 to 107 wherein the organic solvent comprises xylenes.

Embodiment 109 is the process of any one of embodiments 100 to 108 wherein the organic solvent comprises an alkyl, dialkyl ether, or halogenated alkyl solvent.

Embodiment 110 is the process of embodiment 109 wherein the alkyl solvent is selected from the group consisting of hexane, heptane, octane, and mixtures thereof.

Embodiment 111 is the process of embodiment 109 or 110 wherein the dialkyl ether solvent has a general formula of R—O—R', wherein R and R' are each independently a $C_1$-$C_6$ alkyl.

Embodiment 112 is the process of any one of embodiments 109 to 111 wherein the dialkyl ether solvent is selected from the group consisting of methyl butyl ether, dibutyl ether, cyclopentyl methyl ether, and mixtures thereof.

Embodiment 113 is the process of any one of embodiments 100 to 112 wherein the weight ratio of organic solvent to the chlorophenol feed mixture fed to the FLLE zone is from about 1:1 to about 15:1, from about 2:1 to about 10:1, from about 3:1 to about 10:1, or from about 3:1 to about 7:1.

Embodiment 114 is the process of any one of embodiments 100 to 113 wherein the aqueous solution comprising base is fed into a stage that is positioned within an upper portion of the rectifying section.

Embodiment 115 is the process of any one of embodiments 100 to 114 wherein the base comprises an alkali or alkaline earth hydroxide, carbonate, or bicarbonate.

Embodiment 116 is the process of any one of embodiments 100 to 115 wherein the base comprises potassium hydroxide.

Embodiment 117 is the process of embodiment 116 wherein the concentration of potassium hydroxide in the aqueous solution comprising base that is fed to the FLLE zone is from about 1 wt. % to about 10 wt. %, from about 2 wt. % to about 7 wt. %, from about 3 wt. % to about 7 wt. %, from about 3 wt. % to about 5 wt. %, or from about 2 wt. % to about 5 wt. %.

Embodiment 118 is the process of any one of embodiments 100 to 117 wherein the molar ratio of the base to 2,5-dichlorophenol in the chlorophenol feed mixture is from about 0.5:1 to about 5:1, from about 0.5:1 to about 3:1, from about 0.9:1 to about 3:1, from about 1.5:1 to about 3:1, or from about 2:1 to about 3:1.

Embodiment 119 is the process of any one of embodiments 100 to 118 further comprising feeding an aqueous solution comprising acid to the stripping section of the FLLE zone.

Embodiment 120 is the process of embodiment 119 wherein the aqueous solution comprising acid is fed into a stage that is positioned within a lower portion of the stripping section in the FLLE zone.

Embodiment 121 is the process of embodiment 120 wherein the aqueous solution comprising acid is fed into a stage that is positioned in the lower 5% to 25%, 10% to 25%, or 10% to 20% of the stripping section.

Embodiment 122 is the process of any one of embodiments 119 to 121 wherein the acid is a mineral acid or an organic acid.

Embodiment 123 is the process of embodiment 122 wherein the mineral acid is selected from the group consisting of hydrochloric acid, sulfuric acid, and phosphoric acid.

Embodiment 124 is the process of embodiment 122 wherein the organic acid is selected from the group consisting of formic acid, acetic acid, propionic acid, butyric acid, citric acid and mixtures thereof.

Embodiment 125 is the process of any one of embodiments 119 to 121 wherein the acid comprises hydrochloric acid.

Embodiment 126 is the process of embodiment 125 wherein the concentration of hydrochloric acid in the aqueous solution that is fed to the FLLE zone is from about 5 wt. % to about 30 wt. %, from about 10 wt. % to about 30 wt. %, from about 15 wt. % to about 30 wt. %, from about 20 wt. % to about 30 wt. %, from about 25 wt. % to about 30 wt. %, from about 10 wt. % to about 25 wt. %, from about 15 wt. % to about 25 wt. %, or from about 20 wt. % to about 25 wt. %.

Embodiment 127 is the process of any one of embodiments 119 to 126 wherein the molar ratio of acid to base is from about 0.5:1 to about 2:1, from about 0.5:1 to about 1:1, or from about 0.6:1 to about 0.8:1.

Embodiment 128 is the process of any one of embodiments 1 to 127 wherein the pH of the aqueous extract comprising 2,5-dichlorophenol and/or a salt thereof in the aqueous phase exiting the stripping section is maintained between about 8 and about 9, between about 8.2 and about 8.8, or between about 8.4 and about 8.8.

Embodiment 129 is the process of any one of embodiments 100 to 128 wherein the pH of the aqueous phase contacting the organic extract comprising 2,4-dichlorophenol in the organic phase exiting the rectifying section is greater than the pH of the aqueous extract comprising 2,5-dichlorophenol and/or a salt thereof in the aqueous phase exiting the stripping section.

Embodiment 130 is the process of any one of embodiments 100 to 129 wherein the pH of the aqueous phase contacting the organic extract comprising 2,4-dichlorophenol in the organic phase exiting the rectifying section is between about 9 and about 10.5, between about 9.5 and about 10.5, or between about 9.5 and about 10.

Embodiment 131 is the process of any one of embodiments 100 to 130 wherein the weight ratio of 2,4-dichlorophenol to 2,5-dichlorophenol in the chlorophenol feed mixture to the FLLE zone is from about 10:1 to about 200:1, from about 10:1 to about 100:1, from about 10:1 to about 50:1, from about 20:1 to about 200:1, from about 20:1 to about 100:1, or from about 20:1 to about 50:1.

Embodiment 132 is the process of any one of embodiments 100 to 131 wherein the chlorophenol feed mixture further comprises at least one monochlorophenol selected from the group consisting of 2-monochlorophenol, 4-monochlorophenol, and combinations thereof.

Embodiment 133 is the process of any one of embodiments 100 to 132 wherein the chlorophenol feed mixture further comprises 2,6-dichlorophenol and/or 2,4,6-trichlorophenol.

Embodiment 134 is the process of any one of embodiments 100 to 133 wherein the 2,4-dichlorophenol concentration in the chlorophenol feed mixture is at least about 50 wt. %, at least about 60 wt. %, at least about 70 wt. %, at least about 80 wt. %, or at least about 90 wt. % of the total chlorophenol content.

Embodiment 135 is the process of any one of embodiments 100 to 134 wherein the 2,4-dichlorophenol concentration in the chlorophenol feed mixture is from about 50 wt. % to about 95 wt. %, from about 50 wt. % to about 90 wt. %, from about 50 wt. % to about 80 wt. %, from about 60 wt. % to about 95 wt. %, from about 60 wt. % to about 90 wt. %, from about 60 wt. % to about 80 wt. %, from about 70 wt. % to about 95 wt. %, from about 70 wt. % to about 90 wt. %, from about 70 wt. % to about 80 wt. %, from about 80 wt. % to about 95 wt. %, or from about 80 wt. % to about 90 wt. % of the total chlorophenol content.

Embodiment 136 is the process of any one of embodiments 100 to 135 wherein the 2,5-dichlorophenol concentration in the chlorophenol feed mixture is less than about 10 wt. %, or less than about 5 wt. % of the total chlorophenol content.

Embodiment 137 is the process of any one of embodiments 100 to 136 wherein the 2,5-dichlorophenol concentration in the chlorophenol feed mixture is from about 0.5 wt. % to about 10 wt. %, from about 0.5 wt. % to about 5 wt. %, from about 1 wt. % to about 10 wt. %, from about 1 wt. % to about 5 wt. %, or from about 5 wt. % to about 10 wt. % of the total chlorophenol content.

Embodiment 138 is the process of any one of embodiments 100 to 137 wherein the 2,4-dichlorophenol content in the organic extract is at least about 60 wt. %, at least about 70 wt. %, at least about 80 wt. %, or at least about 90 wt. % of the total chlorophenol content in the organic extract.

Embodiment 139 is the process of any one of embodiments 100 to 138 wherein the 2,4-dichlorophenol content in the organic extract is from about 60 wt. % to about 99 wt. %, from about 60 wt. % to about 95 wt. %, from about 60 wt. % to about 90 wt. %, from about 70 wt. % to about 99 wt. %, from about 70 wt. % to about 95 wt. %, from about 70 wt. % to about 90 wt. %, from about 70 wt. % to about 85 wt. %, from about 75 wt. % to about 99 wt. %, from about 75 wt. % to about 95 wt. %, from about 75 wt. % to about 90 wt. %, from about 80 wt. % to about 99 wt. %, from about 80 wt. % to about 95 wt. % or from about 80 wt. % to about 90 wt. % of the total chlorophenol content in the organic extract.

Embodiment 140 is the process of any one of embodiments 100 to 139 wherein the weight ratio of 2,4-dichlorophenol to 2,5-dichlorophenol in the organic extract is at least about 20:1, at least about 50:1, at least about 100:1, or at least about 200:1.

Embodiment 141 is the process of any one of embodiments 100 to 140 wherein the weight ratio of 2,4-dichlorophenol to 2,5-dichlorophenol in the organic extract is from about 20:1 to about 500:1, from about 20:1 to about 200:1, from about 20:1 to about 100:1, from about 20:1 to about 50:1, from about 50:1 to about 500:1, from about 50:1 to about 200:1, from about 50:1 to about 100:1, from about 100:1 to about 500:1, or from about 100:1 to about 200:1.

Embodiment 142 is the process of any one of embodiments 100 to 141 wherein the organic extract further comprises at least one monochlorophenol selected from the group consisting of 2-monochlorophenol, 4-monochlorophenol, and combinations thereof.

Embodiment 143 is the process of any one of embodiments 100 to 142, further comprising feeding the organic extract comprising 2,4-dichlorophenol in the organic phase to a 2,4-dichlorophenol recovery zone to separate the 2,4-dichlorophenol from the organic phase to form a concentrated fraction comprising the 2,4-dichlorophenol and an organic fraction comprising the organic solvent.

Embodiment 144 is the process of embodiment 143 wherein the 2,4-dichlorophenol recovery zone comprises distilling the organic extract comprising 2,4-dichlorophenol in the organic phase.

Embodiment 145 is the process of any one of embodiments 100 to 144 wherein at least a portion of the 2,4-dichlorophenol obtained from the organic extract removed from the FLLE zone is further converted to 2,4-dichlorophenoxyacetic acid or salt or ester thereof.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above processes without departing from the scope of the invention, it is intended that all matter contained in the above description and shown in the accompanying drawings shall be interpreted as illustrative and not in a limiting sense.

What is claimed is:

1. A process for producing an aqueous extract comprising 2,5-dichlorophenol and/or a salt thereof, the process comprising:
    feeding a chlorophenol feed mixture comprising 2,5-dichlorophenol and 2,4-dichlorophenol to a fractional liquid-liquid extraction (FLLE) zone comprising a rectifying section and a stripping section;
    feeding an organic solvent to the stripping section of the FLLE zone;
    feeding an aqueous solution comprising base to the rectifying section of the FLLE zone;
    contacting the feed mixture with the organic solvent and the aqueous solution comprising base in the FLLE zone, wherein at least a portion of the 2,5-dichlorophenol is transferred to an aqueous phase and at least a portion of the 2,4-dichlorophenol is transferred to an organic phase comprising the organic solvent;
    feeding an aqueous solution comprising acid into the stripping section of the FLLE zone;
    removing the aqueous extract comprising 2,5-dichlorophenol and/or a salt thereof in the aqueous phase from the stripping section of the FLLE zone, wherein the weight ratio of total 2,5-dichlorophenol to total 2,4-dichlorophenol in the aqueous extract is greater than the weight ratio of 2,5-dichlorophenol to 2,4-dichlorophenol in the chlorophenol feed mixture; and
    removing an organic extract comprising 2,4-dichlorophenol in the organic phase from the rectifying section of the FLLE zone.

2. The process of claim 1 wherein the rectifying section and/or the stripping section comprises a series of stages.

3. The process of claim 2 wherein the FLLE zone comprises at least one vertical column having a feed location for the chlorophenol feed mixture and wherein the rectifying section is the portion of the column situated above the feed location and the stripping section is the portion of the column situated beneath the feed location.

4. The process of claim 3 wherein the organic solvent is fed into a stage that is positioned within a lower portion of the stripping section.

5. The process of claim 1 wherein the organic solvent comprises xylenes.

6. The process of claim 3 wherein the aqueous solution comprising base is fed into a stage that is positioned within an upper portion of the rectifying section.

7. The process of claim 1 wherein the base comprises potassium hydroxide.

8. The process of claim 3, wherein the aqueous solution comprising acid is fed into a stage that is positioned with a lower portion of the stripping section.

9. The process of claim 1 wherein the acid comprises hydrochloric acid.

10. The process of claim 1 wherein the molar ratio of acid to base is from about 0.5:1 to about 2:1.

11. The process of claim 1 wherein the pH of the aqueous extract comprising 2,5-dichlorophenol and/or a salt thereof in the aqueous phase exiting the stripping section is maintained between about 8 and about 9.

12. The process of claim 1 wherein the pH of the aqueous phase contacting the organic extract comprising 2,4-dichlorophenol in the organic phase exiting the rectifying section is greater than the pH of the aqueous extract comprising 2,5-dichlorophenol and/or a salt thereof in the aqueous phase exiting the stripping section.

13. The process of claim 1 wherein the pH of the aqueous phase contacting the organic extract comprising 2,4-dichlorophenol in the organic phase exiting the rectifying section is between about 9 and about 10.5.

14. The process of claim 1 wherein the weight ratio of 2,4-dichlorophenol to 2,5-dichlorophenol in the chlorophenol feed mixture to the FLLE zone is from about 1:1 to about 5:1.

15. The process of claim 1 wherein the chlorophenol feed mixture further comprises 2-, 3-, 4-monochlorophenol, 2,6-dichlorophenol, 3,4-dichlorophenol, and/or 2,3-dichlorophenol.

16. The process of claim 1 wherein the total 2,5-dichlorophenol content in the aqueous extract is from about 55 wt. % to about 99 wt. % of the total chlorophenol content in the aqueous extract.

17. The process of claim 1 wherein the weight ratio of total 2,5-dichlorophenol to total 2,4-dichlorophenol in the aqueous extract is from about 10:1 to 200:1.

18. The process of claim 1 wherein the aqueous extract comprising 2,5-dichlorophenol and/or a salt thereof in the aqueous phase further comprises 2,6-dichlorophenol and/or a salt thereof, and wherein the total content of 2,6-dichlorophenol is no more than about 3 wt. % of the total chlorophenol content of the aqueous extract.

19. The process of claim 1 wherein the aqueous extract comprising 2,5-dichlorophenol and/or a salt thereof in the aqueous phase further comprises 2,3-dichlorophenol and/or a salt thereof, and wherein the total content of 2,3-dichlorophenol is no more than about 1 wt. % of the total chlorophenol content of the aqueous extract.

20. The process of claim 1, further comprising:
    carboxylating at least a portion of 2,5-dichlorophenol or salt thereof obtained from the aqueous extract removed from the FLLE zone to form 2-hydroxy-3,6-dichlorobenzoic acid or salt thereof;
    methylating 2-hydroxy-3,6-dichlorobenzoic acid or salt thereof with a methylating agent to form 3,6-dichloro-2-methoxybenzoic acid or salt thereof and/or methyl 3,6-dichloro-2-methyoxybenzoate; and
    when methyl 3,6-dichloro-2-methyoxybenzoate is formed, saponifying methyl 3,6-dichloro-2-methyoxybenzoate with a base to form a salt of 3,6-dichloro-2-methoxybenzoic acid.

* * * * *